(12) United States Patent
Schmidt et al.

(10) Patent No.: US 8,945,591 B2
(45) Date of Patent: *Feb. 3, 2015

(54) METHODS AND COMPOSITIONS INVOLVING IMMUNOSTIMULATORY OLIGODEOXYNUCLEOTIDES

(71) Applicant: Intercell AG, Vienna (AT)

(72) Inventors: Walter Schmidt, Vienna (AT); Karen Lingnau, Vienna (AT); Carola Wenander, Vienna (AT); Alena Egyed, Vienna (AT)

(73) Assignee: Valneva Austria GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/786,815

(22) Filed: Mar. 6, 2013

(65) Prior Publication Data

US 2013/0183339 A1    Jul. 18, 2013

Related U.S. Application Data

(63) Continuation of application No. 10/297,555, filed as application No. PCT/EP01/06433 on Jun. 7, 2001, now Pat. No. 8,568,742.

(30) Foreign Application Priority Data

Jun. 8, 2000 (AT) ................. A 1000/2000
Nov. 23, 2000 (AT) ................. A 1973/2000

(51) Int. Cl.
   *A61K 45/00* (2006.01)
   *A61K 48/00* (2006.01)
   *C07H 21/02* (2006.01)
   *C07H 21/04* (2006.01)

(52) U.S. Cl.
   USPC ....... 424/278.1; 424/184.1; 514/44; 536/23.1

(58) Field of Classification Search
   None
   See application file for complete search history.

(56) References Cited

U.S. PATENT DOCUMENTS

| | | | |
|---|---|---|---|
| 3,725,545 | A | 4/1973 | Maes |
| 3,906,092 | A | 9/1975 | Hilleman et al. |
| 5,646,262 | A | 7/1997 | Korba et al. |
| 5,691,136 | A | 11/1997 | Lupski et al. |
| 5,814,491 | A | 9/1998 | Vijg et al. |
| 7,148,191 | B2 | 12/2006 | Egyed et al. |
| 7,704,514 | B2 | 4/2010 | Buschle et al. |
| 7,951,845 | B2 | 5/2011 | Miller et al. |
| 2002/0081577 | A1 | 6/2002 | Kilkuskie et al. |
| 2002/0132995 | A1 | 9/2002 | Agrawal et al. |

FOREIGN PATENT DOCUMENTS

| | | |
|---|---|---|
| CA | 2 407 942 A1 | 11/2001 |
| WO | WO-90/14424 A1 | 11/1990 |
| WO | WO-92/11389 A1 | 7/1992 |
| WO | WO-94/19945 A1 | 9/1994 |
| WO | WO-98/14611 A2 | 4/1998 |
| WO | WO-98/16247 A1 | 4/1998 |
| WO | WO-98/55495 A2 | 12/1998 |
| WO | WO-98/55609 A1 | 12/1998 |
| WO | WO-99/67285 A1 | 12/1999 |
| WO | WO-01/22972 A2 | 4/2001 |

OTHER PUBLICATIONS

Alvarez-Bravo et al., Mode of action of an antibacterial peptide, KLKLLLLLKLK-NH2. J Biochem. Jun. 1995;117(6):1312-6.
Andreu and Rivas, "Animal antimicrobial peptides: an overview," Biopoly, 47:415-433, 1998.
Ballas et al., "Induction of NK activity in murine and human cells by CpG motifs in oligodeoxynucleotides and bacterial DNA," J. of Immunology, 157:1840-1845, 1996.
Bann et al. Induction of NK activity in murine and human cells by CpG motifs in oligodeoxynucleotides and bacterial DNA. J. Immunol., 1996, vol. 157, 1840-1845.
Bloom et al., "Identification of tyrosinase-related protein 2 as a tumor rejection antigen for the B16 melanoma," I of Exp. Med., 185:453-459, 1997.
Buschle et al., "Chemically defined, cell-free cancer vaccines: use of tumor antigen-derived peptides or polyepitope proteins for vaccination," Gene Ther. Mol. Biol., 1:309-321, 1998.

(Continued)

*Primary Examiner* — Oluwatosin Ogunbiyi
(74) *Attorney, Agent, or Firm* — Wolf, Greenfield & Sacks, P.C.

(57) ABSTRACT

Described is an immunostimulatory oligodeoxynucleic acid molecule (ODN) having the structure according to formula (I), wherein any NMP is a 2' deoxynucleoside monophosphate or monothiophosphate, selected from the group consisting of deoxyadenosine-, deoxyguanosine-, deoxyinosine-, deoxycytosine-, deoxyuridine-, deoxythymidine-, 2-methyl-deoxyinosine-, 5-methyl-deoxycytosine-, deoxypseudouridine-, deoxyribosepurine-, 2-amino-deoxyribosepurine-, -6-S-deoxyguanine-, 2-dimethyl-deoxyguanosine- or N-isopentenyl-deoxyadenosine-monophosphate or -monothiophosphate, NUC is a 2' deoxynucleoside, selected from the group consisting of deoxyadenosine-, deoxyguanosine-, deoxyinosine-, deoxycytosine-, deoxyuridine-, deoxythymidine-, 2-methyl-deoxyinosine-, 5-methyl-deoxycytosine-, deoxypseudouridine-, deoxyribosepurine-, 2-amino-deoxyribosepurine-, 6-S-deoxyguanine-, 2-dimethyl-deoxyguanosine- or N-isopentenyl-deoxyadenosine, any X is O or S, a and b are integers from 0 to 100 with the proviso that a+b is between 4 and 150, B and E are common groups for 5' or 3' ends of nucleic acid molecules, as well as a pharmaceutical composition containing such ODNs.

14 Claims, 9 Drawing Sheets

(56) References Cited

OTHER PUBLICATIONS

Buschle et al., "Transloading of tumor antigen-derived peptides into antigen-presenting cells," Proc. Natl. Acad. Sci., USA, 94:3256-3261, 1997.

Canadian Office Action, issued in Canadian Application No. 2,411,575, mailed Feb. 10, 2010.

Cavanaugh et al., The activation of murine macrophages and natural killer cells by the partially thiolated double stranded RNA poly(I)-mercapto Poly (C), Research Communications in Molecular Pathology and Pharmacology, 91:131-147, 1996.

Davis, "CpG DNA is a potent enhancer of specific immunity in mice immunized with recombinant hepatitis B surface antigen,".I. of Immunology, 160:870-876, 1998.

Deng et al., "Intra-articularly localized bacterial DNA containing CpG motifs inducts arthritis," Nat. Medicine, 5:702-705, 1999.

Ganz and Lehrer, "Antibiotic peptides from higher eukaryotes: biology and applications," Molecular Medicine Today, 5:292-297, 1999.

Ganz, "Enhanced: defensins and host defense," Science, 286:420-421, 1999.

Hancock, "Host defence (cationic) peptides. What is their future clinical potential?" Drugs, 57:469-473, 1999.

Hartmann et al. Delineation of a CpG phosphorothioate oligodeoxynucleotide for activating primate immune responses in vitro and in vivo. Journal of Immunology, 2000, vol. 164, pp. 1617-1624.

Hartmann, "CpG DNA: a potent signal for growth, activation, and maturation of human dendritic cells," Proc. Natl, Acad. Sci., USA, 96:9305-9310, 1999.

Hoffmann et al., "Phylogenetic perspectives in inmte immunity," Science, 284:1313-1317, 1999.

Klinrnan et al., "CpG motifs present in bacterial DNA rapidly induce lymphocytes to secrete interleukin 6, interleukin 12, and interferon y," Proc. Natl. Acad. Sci., USA, 93:2879-2883, 1996.

Krieg et al. CpG motifs in bacterial DNA trigger direct B-cell activation. Nature, 1995;374:546-549.

Krieg et al., "The role of CpG dinucleotides in DNA vaccines," Trends in Microbiology, 6:23-27, 1998.

Krieg, "CpG DNA: a novel immunomodulator," Trends in Microbiology, 7:64, 1999.

Lethe, "Mouse tumor rejection antigens P815A and P815B: two epitopes carried by a single peptide," Eur. J. Iinmunol., 22:2283-2288, 1992.

Liljeqvist and Stahl, "Production of recombinant subunit vaccines; protein immunogens, live delivery systems and nucleic acid vaccines," J. of Biotechnology, 73:1-33, 1999.

Lipford et al., "Bacterial DNA as immune cell activator," Trends in Microbiology, 6:496-500, 1998.

Manetti et al., "Polyinosinic acid: polycytidylic acid promotes T helper type 1-specific immune response by stimulating macrophage production of interferon-a and interleukin-12," Eur J. Immunol., 25:2656-2660, 1995.

Miura et al. Use of the deoxyinosine-containing probe to isolate and sequence cDNA encoding the fusion (F) glycoprotein of Sendai virus (HVJ). Gene. 1985;38(1-3):271-4.

Office Action, issued in Norwegian Patent App. No. 20025835, mailed Dec. 17, 2009. (English Translation).

Oxenius et al., "CpG-containing oligonucleotides are efficient adjuvants for induction of protective antiviral immune responses with T-cell peptide vaccines," J of Virology, 73:4120-4126, 1999.

Parronchi et al., "Phoshphorothioate oligodeoxynucleotides promote the in vitro development of human allergen-specific CD4+ T cells into Thl effectors,"J of Immunology, 163:5946-5953, 1999.

Pisetsky, "Immunostirnulatory DNA: a clear and present danger?" Nature Medicine, 3:829831, 1997.

Rodrigues et al., "The in vivo cytotoxic activity of CD8+ T cell clones correlates with their levels of expression of adhesion molecules," J. Exp. Med., 175:895-905, 1992.

Schmidt et al., "Cell-free tumor antigen peptide-based cancer vaccines," Proc. Natl. Acad. Sci., USA, 94:3262-3267, 1997.

Simmaco et al., "Antimicrobial peptides form amphibian skin: what do they tell us?" Biopolymers, 47:435-450, 1998.

Sparbier and Walden, "T cell receptor specificity and mimotopes," Current Opinion in Immunology, 11:214-218, 1999.

Sparwasser et al., "Bacterial DNA and immunostimulatory CpG oligonucleotides trigger maturation and activation of murine dendritic cells," Eur. J. Immunol., 28:2045-2054, 1998.

Sparwasser et al., "Bacterial DNA causes septic shock," Nature, 386:336-337, 1997.

Sparwasser et al., "Macrophages sense pathogens via DNA motifs: induction of tumor necrosis factor-a-mediated shock," Eur. J. ImInunol., 27:1671-1679, 1997.

Wagner et al. Molecular cloning and tissue-specific RNA processing of a murine receptor-type protein tyrosine phosphatase. Eur. J. Biochem. 1994, vol. 226, 773-782.

Weiner et al., "Immunostimulatory oligodeoxynucleotides containing the CpG motif are effective as immune adjuvants in tumor aniigen immunization," Proc. Natl. Acad. Sci., USA, 94:10833-10837, 1997.

Woo et al. G/C-modified oligodeoxynucleotides with selective complementarity: synthesis and hybridization properties. Nucleic Acids Res. Jul. 1, 1996;24(13):2470-5.

SEQUENCE LISTING

```
<160> NUMBER OF SEQ ID NOS: 30

<210> SEQ ID NO 1
<211> LENGTH: 6
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (4)..(4)
<223> OTHER INFORMATION: inosine
<220> FEATURE:
<221> NAME/KEY: misc_feature
<222> LOCATION: (4)..(4)
<223> OTHER INFORMATION: n is a, c, g, or t
```

```
<400> SEQUENCE: 1 gacntt                                                                    6

<210> SEQ ID NO 2
<211> LENGTH: 6
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (1)..(4)
<223> OTHER INFORMATION: inosine
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 2 nacntt                                                                    6

<210> SEQ ID NO 3
<211> LENGTH: 6
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t

<400> SEQUENCE: 3 ganctt                                                                    6

<210> SEQ ID NO 4
<211> LENGTH: 6
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (1)..(3)
<223> OTHER INFORMATION: inosine
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t

<400> SEQUENCE: 4 nanctt                                                                    6

<210> SEQ ID NO 5
<211> LENGTH: 36
<212> TYPE: PRT
<213> ORGANISM: Mus musculus
<220> FEATURE:
<221> NAME/KEY: MOD_RES
```

-continued

```
<222> LOCATION: (22)..(22)
<223> OTHER INFORMATION: X = any natural occuring amino acid

<400> SEQUENCE: 5

Arg Leu Ala Gly Leu Arg Lys Gly Gly Glu Lys Ile Gly Glu Lys
1               5                   10                  15

Leu Lys Lys Ile Gly Xaa Lys Ile Lys Asn Phe Phe Gln Lys Leu Val
                20                  25                  30

Pro Gln Pro Glu
        35

<210> SEQ ID NO 6
<211> LENGTH: 8
<212> TYPE: PRT
<213> ORGANISM: Artificial
<220> FEATURE:
<223> OTHER INFORMATION: Epitope

<400> SEQUENCE: 6

Ser Ile Ile Asn Phe Glu Lys Leu
1               5

<210> SEQ ID NO 7
<211> LENGTH: 20
<212> TYPE: DNA
<213> ORGANISM: Artificial
<220> FEATURE:
<223> OTHER INFORMATION: ODN

<400> SEQUENCE: 7
tccatgacgt tcctgatgct                                             20

<210> SEQ ID NO 8
<211> LENGTH: 8
<212> TYPE: PRT
<213> ORGANISM: Artificial
<220> FEATURE:
<223> OTHER INFORMATION: Epitope

<400> SEQUENCE: 8

Val Tyr Asp Phe Phe Val Trp Leu
1               5

<210> SEQ ID NO 9
<211> LENGTH: 17
<212> TYPE: DNA
<213> ORGANISM: Artificial
<220> FEATURE:
<223> OTHER INFORMATION: ODN

<400> SEQUENCE: 9
atgacgttcc tgatgct                                                17

<210> SEQ ID NO 10
<211> LENGTH: 20
<212> TYPE: DNA
<213> ORGANISM: Artificial
<220> FEATURE:
<223> OTHER INFORMATION: ODN
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (9)..(9)
<223> OTHER INFORMATION: inosine
```

-continued

```
<220> FEATURE:
<221> NAME/KEY: modified_base
<222> LOCATION: (9)..(9)
<223> OTHER INFORMATION: n = inosine
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 10
nhhhhhwdnn hhhhhhhhwn                                               20

<210> SEQ ID NO 11
<211> LENGTH: 20
<212> TYPE: DNA
<213> ORGANISM: Artificial
<220> FEATURE:
<223> OTHER INFORMATION: ODN
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (6)..(6)
<223> OTHER INFORMATION: n = inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (8)..(8)
<223> OTHER INFORMATION: inosine
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: modified_base
<222> LOCATION: (15)..(15)
<223> OTHER INFORMATION: inosine
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: modified_base
<222> LOCATION: (18)..(18)
<223> OTHER INFORMATION: inosine
<220> FEATURE:
<221> NAME/KEY: misc_feature
<222> LOCATION: (18)..(19)
<223> OTHER INFORMATION: n is a, c, g, or t

<400> SEQUENCE: 11
nhhwdndnnh hhhdnndnnh                                               20

<210> SEQ ID NO 12
<211> LENGTH: 20
<212> TYPE: DNA
<213> ORGANISM: Artificial
<220> FEATURE:
<223> OTHER INFORMATION: ODN
<220> FEATURE:
<221> NAME/KEY: misc_feature
<222> LOCATION: (1)..(1)
```

```
<223> OTHER INFORMATION: n is a, c, g, or t
<220> FEATURE:
<221> NAME/KEY: modified_base
<222> LOCATION: (9)..(9)
<223> OTHER INFORMATION: inosine
<220> FEATURE:
<221> NAME/KEY: modified_base
<222> LOCATION: (9)..(9)
<223> OTHER INFORMATION: n = inosine
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 12
nhhhhhwdnd hhhhhhhhwn                                          20

<210> SEQ ID NO 13
<211> LENGTH: 20
<212> TYPE: DNA
<213> ORGANISM: Artificial
<220> FEATURE:
<223> OTHER INFORMATION: ODN
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (6)..(6)
<223> OTHER INFORMATION: n = inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (8)..(8)
<223> OTHER INFORMATION: inosine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (15)..(15)
<223> OTHER INFORMATION: inosine
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (18)..(18)
<223> OTHER INFORMATION: inosine
<220> FEATURE:
<221> NAME/KEY: misc_feature
<222> LOCATION: (18)..(18)
<223> OTHER INFORMATION: n is a, c, g, or t

<400> SEQUENCE: 13
nhhwdndndh hhhdnddndh                                          20

<210> SEQ ID NO 14
<211> LENGTH: 20
<212> TYPE: DNA
<213> ORGANISM: Artificial
```

<220> FEATURE:
<223> OTHER INFORMATION: ODN
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (6)..(6)
<223> OTHER INFORMATION: n = inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: inosine
<220> FEATURE:
<221> NAME/KEY: misc_feature
<222> LOCATION: (9)..(9)
<223> OTHER INFORMATION: n is a, c, g, or t

<400> SEQUENCE: 14
tccatnacnt tcctgatgct                                               20

<210> SEQ ID NO 15
<211> LENGTH: 20
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (9)..(9)
<223> OTHER INFORMATION: n = inosine
<220> FEATURE:
<221> NAME/KEY: misc_feature
<222> LOCATION: (9)..(9)
<223> OTHER INFORMATION: n is a, c, g, or t

<400> SEQUENCE: 15
tccatgacnt tcctgatgct                                               20

<210> SEQ ID NO 16
<211> LENGTH: 20
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (6)..(6)
<223> OTHER INFORMATION: inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: inosine
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (15)..(15)
<223> OTHER INFORMATION: inosine
<220> FEATURE:
<221> NAME/KEY: misc_feature
<222> LOCATION: (15)..(15)
<223> OTHER INFORMATION: n is a, c, g, or t
<220> FEATURE:

```
<221> NAME/KEY: modified_base
<222> LOCATION: (18)..(18)
<223> OTHER INFORMATION: inosine
<220> FEATURE:
<221> NAME/KEY: misc_feature
<222> LOCATION: (18)..(18)
<223> OTHER INFORMATION: n is a, c, g, or t

<400> SEQUENCE: 16
tccatnacnt tcctnatnct                                               20

<210> SEQ ID NO 17
<211> LENGTH: 20
<212> TYPE: DNA
<213> ORGANISM: Artificial
<220> FEATURE:
<223> OTHER INFORMATION: ODN

<400> SEQUENCE: 17
tccatgagct tcctgatgct                                               20

<210> SEQ ID NO 18
<211> LENGTH: 20
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (8)..(8)
<223> OTHER INFORMATION: n = inosine
<220> FEATURE:
<221> NAME/KEY: misc_feature
<222> LOCATION: (8)..(8)
<223> OTHER INFORMATION: n is a, c, g, or t

<400> SEQUENCE: 18
tccatganct tcctgatgct                                               20

<210> SEQ ID NO 19
<211> LENGTH: 20
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (6)..(6)
<223> OTHER INFORMATION: n = inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (8)..(8)
<223> OTHER INFORMATION: n = inosine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (15)..(15)
<223> OTHER INFORMATION: n = inosine
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (18)..(18)
<223> OTHER INFORMATION: n = inosine
```

```
<220> FEATURE:
<221> NAME/KEY: misc_feature
<222> LOCATION: (18)..(18)
<223> OTHER INFORMATION: n is a, c, g, or t

<400> SEQUENCE: 19
tccatnanct tcctnatnct                                                    20

<210> SEQ ID NO 20
<211> LENGTH: 19
<212> TYPE: DNA
<213> ORGANISM: Artificial
<220> FEATURE:
<223> OTHER INFORMATION: ODN
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (9)..(9)
<223> OTHER INFORMATION: n = inosine
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 20
nhhhhhwdnh hhhhhhhwn                                                     19

<210> SEQ ID NO 21
<211> LENGTH: 20
<212> TYPE: DNA
<213> ORGANISM: Artificial
<220> FEATURE:
<223> OTHER INFORMATION: ODN
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (6)..(6)
<223> OTHER INFORMATION: n = inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (8)..(8)
<223> OTHER INFORMATION: n = inosine
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: modified_base
<222> LOCATION: (15)..(15)
<223> OTHER INFORMATION: n = inosine
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: modified_base
<222> LOCATION: (18)..(18)
<223> OTHER INFORMATION: n = inosine
<220> FEATURE:
<221> NAME/KEY: misc_feature
<222> LOCATION: (18)..(19)
```

<223> OTHER INFORMATION: n is a, c, g, or t

<400> SEQUENCE: 21
nhhwdndnnh hhhdnndnnh                                           20

<210> SEQ ID NO 22
<211> LENGTH: 20
<212> TYPE: DNA
<213> ORGANISM: Artificial
<220> FEATURE:
<223> OTHER INFORMATION: ODN
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (9)..(9)
<223> OTHER INFORMATION: n = inosine
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 22
nhhhhhwdnd hhhhhhhhwn                                           20

<210> SEQ ID NO 23
<211> LENGTH: 20
<212> TYPE: DNA
<213> ORGANISM: Artificial
<220> FEATURE:
<223> OTHER INFORMATION: ODN
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (6)..(6)
<223> OTHER INFORMATION: n = inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (8)..(8)
<223> OTHER INFORMATION: n = inosine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (15)..(15)
<223> OTHER INFORMATION: n = inosine
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (18)..(18)
<223> OTHER INFORMATION: n = inosine
<220> FEATURE:
<221> NAME/KEY: misc_feature
<222> LOCATION: (18)..(18)
<223> OTHER INFORMATION: n is a, c, g, or t

<400> SEQUENCE: 23

-continued nhhwdndndh hhhdnddndh                                             20

<210> SEQ ID NO 24
<211> LENGTH: 3
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (3)..(3)
<223> OTHER INFORMATION: n = inosine
<220> FEATURE:
<221> NAME/KEY: misc_feature
<222> LOCATION: (3)..(3)
<223> OTHER INFORMATION: n is a, c, g, or t

<400> SEQUENCE: 24 wdn                                                                3

<210> SEQ ID NO 25
<211> LENGTH: 4
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (3)..(3)
<223> OTHER INFORMATION: n = inosine
<220> FEATURE:
<221> NAME/KEY: misc_feature
<222> LOCATION: (3)..(3)
<223> OTHER INFORMATION: n is a, c, g, or t

<400> SEQUENCE: 25 wdnd                                                               4

<210> SEQ ID NO 26
<211> LENGTH: 6
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (3)..(3)
<223> OTHER INFORMATION: n = inosine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: n = inosine
<220> FEATURE:
<221> NAME/KEY: misc_feature
<222> LOCATION: (5)..(6)
<223> OTHER INFORMATION: n is a, c, g, or t

<400> SEQUENCE: 26 wdndnn                                                             6

<210> SEQ ID NO 27
<211> LENGTH: 6
<212> TYPE: DNA
<213> ORGANISM: Artificial
<220> FEATURE:
<223> OTHER INFORMATION: ODN
<220> FEATURE:

```
<221> NAME/KEY: modified_base
<222> LOCATION: (3)..(3)
<223> OTHER INFORMATION: n = inosine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: n = inosine
<220> FEATURE:
<221> NAME/KEY: misc_feature
<222> LOCATION: (5)..(5)
<223> OTHER INFORMATION: n is a, c, g, or t

<400> SEQUENCE: 27 wdndnd                                                                      6

<210> SEQ ID NO 28
<211> LENGTH: 10
<212> TYPE: DNA
<213> ORGANISM: Artificial
<220> FEATURE:
<223> OTHER INFORMATION: ODN
<220> FEATURE:
<221> NAME/KEY: modified_base
<222> LOCATION: (6)..(6)
<223> OTHER INFORMATION: n = inosine
<220> FEATURE:
<221> NAME/KEY: misc_feature
<222> LOCATION: (6)..(6)
<223> OTHER INFORMATION: n is a, c, g, or t

<400> SEQUENCE: 28 hhhwdndhhh                                                                 10

<210> SEQ ID NO 29
<211> LENGTH: 10
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n = inosine

<400> SEQUENCE: 29 hhhwdndhhh                                                                 10

<210> SEQ ID NO 30
<211> LENGTH: 26
<212> TYPE: DNA
<213> ORGANISM: Artificial Sequence
<220> FEATURE:
<223> OTHER INFORMATION: oligo-dIC26-mer
<220> FEATURE:
<221> NAME/KEY: misc_feature
<222> LOCATION: (1)..(26)
<223> OTHER INFORMATION: n is deoxyinosine
<220> FEATURE:
<221> NAME/KEY: misc_feature
<222> LOCATION: (1)..(26)

<400> SEQUENCE: 30
ncncncncnc ncncncncnc ncncnc                                               26
```

METHODS AND COMPOSITIONS INVOLVING IMMUNOSTIMULATORY OLIGODEOXYNUCLEOTIDES

This application is continuation of U.S. patent application Ser. No. 10/297,555, filed Dec. 6, 2002, which is a U.S. national phase application under 35 U.S.C. §371 of PCT Application No. PCT/EP01/06433 filed Jun. 7, 2001, which claims priority to Austrian Application Nos. A 1973/2000 filed Nov. 23, 2000 and A 1000/2000 filed Jun. 8, 2000, the entire texts of which are specifically incorporated by reference herein without disclaimer.

The present invention relates to immunostimulatory oligodeoxynucleic molecules (ODNs) and pharmaceutical compositions containing such ODNs.

Vaccines can save more lives (and resources) than any other medical intervention (Nossal, 1998). Owing to worldwide vaccination programs the incidence of many fatal diseases has been decreased drastically. Although this notion is valid for a whole panel of diseases, e.g. tuberculosis, diphtheria, pertussis, measles and tetanus, there are no effective vaccines for numerous infectious disease including most viral infections, such as AIDS. There are also no effective vaccines for other diseases, infectious or non-infectious claiming millions the lives of millions of patients per year including malaria or cancer. In addition, the rapid emergence of antibiotic-resistant bacteria and microorganisms calls for alternative treatments with vaccines being a logical choice. Finally, the great need for vaccines is also illustrated by the fact that infectious diseases, rather than cardiovascular disorders or cancer or injuries remain the largest cause of death and disability in the world (Bloom and Widdus, 1998).

From an immunological point of view one major problem in the field of vaccines today is that traditional vaccines (and/or the immune-modulating compounds contained within these preparations) are designed to induce high levels of antibodies (Harrow and Lane, 1988). However, antibodies on their own are not effective in preventing a large number of diseases including most illnesses caused by viruses, intracellular bacteria, certain parasites and cancer. Examples for such diseases are, but are not restricted to, the above-mentioned HIV virus or *Plasmodium* spec. in case of malaria. In numerous experimental systems it has been shown that the cellular arm of the immune system, including T cells, rather than the humoral arm, is important for these indications. Therefore, novel, innovative technologies are needed to overcome the limitations of conventional vaccines. The focus must be on technologies that reliably induce the cellular immune system, including antigen specific T cells, which recognize molecules expressed on pathogen infected cells. Ideally, vaccines are designed that induce both T cells distinguishing diseased and/or infected cells from normal cells and, simultaneously, antibodies secreted by B cells recognising pathogens in extracellular compartments.

Several established vaccines consist of live attenuated organism where the risk of reversion to the virulent wild-type strain exists. In particular in immunocompromised hosts this can be a live threatening scenario. Alternatively, vaccines are administered as a combination of pathogen-derived antigens together with compounds that induce or enhance immune responses against these antigens (these compounds are commonly termed adjuvant), since these subunit vaccines on their own are generally not effective.

Whilst there is no doubt that the above vaccines are valuable medical treatments, there is the disadvantage that, due to their complexity, severe side effects can be evoked, e.g. to antigens that are contained in the vaccine that display cross-reactivity with molecules expressed by cells of vaccinated individuals. In addition, existing requirements from regulatory authorities, e.g. the World Health Organization (WHO), the Food and Drug Administration (FDA), and their European counterparts, for exact specification of vaccine composition and mechanisms of induction of immunity, are difficult to meet.

Antigen presenting cells belong to the innate immune system, which has evolved as a first line host defense that limits infection early after exposure to microorganisms (Hoffmann et al., 1999). Cells of the innate immune system recognize patterns or relatively non-specific structures expressed on their targets rather than more sophisticated, specific structures which are recognised by the adaptive immune system (Hoffmann et al., 1999). Examples of cells of the innate immune system are macrophages and dendritic cells but also granulocytes (e.g. neutrophils), natural killer cells and others. By contrast, cells of the adaptive immune system recognize specific, antigenic structures, including peptides, in the case of T cells and peptides as well as three-dimensional structures in the case of B cells. The adaptive immune system is much more specific and sophisticated than the innate immune system and improves upon repeat exposure to a given pathogen/antigen. Phylogenetically, the innate immune system is much older and can be found already in very primitive organisms. Nevertheless, the innate immune system is critical during the initial phase of antigenic exposure since, in addition to containing pathogens, cells of the innate immune system, i.e. APCs, prime cells of the adaptive immune system and thus trigger specific immune responses leading to clearance of the intruders. In sum, cells of the innate immune system and in particular APCs play a critical role during the induction phase of immune responses by a) containing infections by means of a primitive pattern recognition system and b) priming cells of the adaptive immune system leading to specific immune responses and memory resulting in clearance of intruding pathogens or of other targets (Roitt et al., 1998). These mechanisms may also be important to clear or contain tumor cells.

As mentioned above, cells of the innate immune system recognise patterns expressed on their respective targets. Examples are lipopolysaccharides (LPS) in the case of Gram-negative bacteria, mycobacterial glycolipids, lipoteichoic acids of Gram-positive bacteria, mannans of yeast and double stranded RNAs of viruses (Hoffmann et al., 1999). In addition they may recognise patterns such as altered glycosylations of proteins on tumor cells.

Recent findings describe DNAs of protozoan or lower eukaryotes as a further pattern recognised by the innate (but possibly also by the adaptive) immune system of mammals (and probably most if not all vertebrates) (Krieg, 1996; Lipford et al., 1998).

The immune system recognises lower organisms including bacteria probably due to structural and sequence usage differences between pathogen and host DNA. In particular short stretches of DNA, derived from non-vertebrates or in form of short synthetic ODNs containing nonmethylated cytosine-guanine dinucleotides (CpG) in a certain base context, are targeted (Krieg et al., 1995). CpG motifs are found at the expected frequency in bacterial DNA but are much less frequent in vertebrate DNA (Lipford et al., 1998; Pisetsky, 1999). In addition, non-vertebrate (i.e. bacterial) CpG motifs are not methylated whereas vertebrate CpG sequences are. These differences between bacterial DNA and vertebrate DNA allow vertebrates to recognise non-vertebrate DNA as a danger signal.

Natural CpG-containing DNA, ODNs, as well as thiophosphate-substituted (exchange of thiophosphate residues for phosphate) ODNs containing CpG motifs (CpG-ODN) are not only potent activators of immune cell proliferation and humoral immune responses (Krieg et al., 1995), but also stimulate strong cellular immune responses (reviewed in Lipford et al., 1998). DNA/ODNs containing non-methylated CpG motifs can directly activate monocytic cells (dendritic cells, macrophages) and B cells. Likely, natural killer (NK) cells are not directly activated but respond to monocyte-derived IL-12 (interleukin 12) with a marked increase in their IFN-γ production (Chace et al., 1997). In consequence, the induction of monocytes and NK cells by CpG DNA promotes the induction of Th1-type responses and the development of cytotoxic T cells.

Ribonucleic acid based on inosine and cytosine, like polyinosinic-polycytidylic acid (poly I:C), is known to promote Th1-specific immune responses. It is known to stimulate macrophages to produce cytokines such as IL-1α and IL-12 (Manetti et al., 1995), it is also known as a potent interferon type 1 inducer (Manetti et al., 1995) and a potent NK cell stimulator (Cavanaugh et al., 1996).

This effect, however, was strictly restricted to ribonucleic acid containing inosine and cytidine residues (WO98/16247).

Investigations by the inventors of the present invention showed that ODNs containing non-methylated CpG motifs, although being efficient in stimulating immune system, have essential disadvantages, especially with respect to specificity (high background) and induction of side effects, such as high systemic INF-α generation. High systemic INF-α release is known to cause toxic shock syndrome, which can cause death of afflicted patients.

It is therefore an object of the present invention to provide suitable novel ODNs which do not have such drastic side effects as ODNs based on CpG sequences. It is a further object to reduce the side effects of pharmaceutical compositions containing known ODNs and to provide safe and efficient well-tolerable pharmaceutical compositions with efficient, immunostimulatory properties which are suitable for vaccination of animals, especially of mammals, including humans.

This object is solved by immunostimulatory oligodeoxynucleic acid molecule (ODN) having the structure according to formula (I)

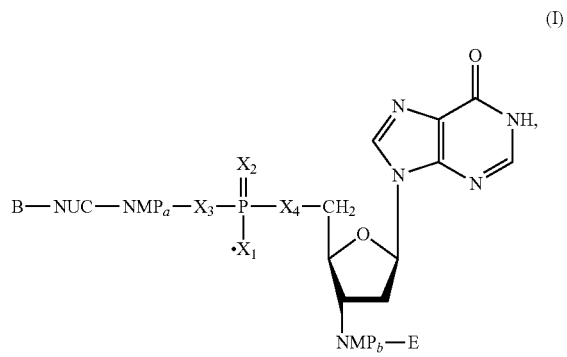

any X is O or S,
wherein
any NMP is a 2' deoxynucleoside monophosphate or monothiophosphate, selected from the group consisting of deoxyadenosine-, deoxyguanosine-, deoxyinosine-, deoxycytosine-, deoxyuridine-, deoxythymidine-, 2-methyl-deoxyinosine-, 5-methyldeoxycytosine-, deoxypseudouridine-, deoxyribosepurine-, 2-amino-deoxyribosepurine-, 6-S-deoxyguanine-, 2-dimethyl-deoxyguanosine- or N-isopentenyl-deoxyadenosine-monophosphate or -monothiophosphat, NUC is a 2' deoxynucleoside, selected from the group consisting of deoxyadenosine-, deoxyguanosine-, deoxyinosine-, deoxycytosine-, deoxyuridine-, deoxythymidine-, 2-methyl-deoxyinosine-, 5-methyl-deoxycytosine-, deoxypseudouridine-, deoxyribosepurine-, 2-amino-deoxyribosepurine-, 6-S-deoxyguanine-, 2-dimethyl-deoxyguanosine- or N-isopentenyl-deoxyadenosine, a and b are integers from 0 to 100 with the proviso that a+b is between 4 and 150, B and E are common groups for 5' or 3' ends of nucleic acid molecules.

Surprisingly it turned out that ODNs containing deoxyinosine residues (I-ODNs) show an immunostimulatory effect comparable or in many instances even better than ODNs containing CpG motifs. Moreover, ODNs according to the present invention produce more specific immune responses to a given antigen or antigen fragment than CpG ODNs. In addition, ODNs according to the present invention reduced the induction of adverse side reactions, especially the induction of systemic TNF-α or IL-6.

Whereas certain immunostimulatory effects had been described for inosine containing RNA molecules, such as poly-IC or the molecules mentioned in WO98/16247, it surprisingly turned out that deoxynucleic acid molecules containing deoxyinosine residues, may be good immunostimulating ODNs.

In addition, the I-ODNs according to the present invention are—in contrast to ODNs based on the specific CpG motif—not dependent on a specific motif or a palindromic sequence as described for the CpG oligonucleotides (see e.g. EP 0 468 520 A2, WO96/02555, WO98/18810, WO98/37919, WO98/40100, WO98/52581, WO99/51259 and WO99/56755, all incorporated herein by reference). Therefore, one group of I-ODNs according to the present invention may preferably contain a CI motif (and therefore ODNs described in these incorporated references, wherein one or more guanosine residues are replaced with deoxyinosine residues are preferred embodiments of the present ODNs). It is not necessary for its principle immunostimulatory property, since I-ODNs with an Inosine not placed in a CI or IC context exhibit immunostimulatory properties as well.

The I-ODN according to the present invention is therefore a DNA molecule containing a deoxyinosine residue which is preferably provided in single stranded form.

The I-ODN according to the present invention may be isolated through recombinant methods or chemically synthesized. In the latter case, the I-ODN according to the present invention may also contain modified oligonucleotides which may be synthesized using standard chemical transformations, such as methylphosphonates or other phosphorous based modified oligonucleotides, such as phosphotriesters, phosphoamidates and phosphorodithioates. Other non-phosphorous based modified oligonucleotides can also be used (Stirchak et al., MAR 17 (1989), 6129-6141), however, monophosphates or monothiophosphates being the preferred 2' deoxynucleoside monophosphate to be used in the present invention.

The NMPs of the I-ODNs according to the present invention are preferably selected from the group consisting of deoxyadenosine-, deoxyguanosine-, deoxyinosine-, deoxycytosine-, deoxyuridine-, deoxythymidine-, 2-methyl-deoxyinosine-, 5-methyldeoxycytosine-monophosphate or -monothiophosphate (as usual, the phosphate or thiophosphate group is 5' of the deoxyribose). Whereas it is essential for the ODNs based on the CpG motif that this motif is unmethylated, this is surprisingly not the case for the ODNs according to the present invention, wherein e.g. 2-methyl-deoxyinosine or 5-methyl-deoxycytosine residues have no general negative effect on immunostimulatory properties of the ODNs according to the present invention. Alternatively, instead of the 2-deoxy-forms of the NMPs, also other, especially inert, groups may be present at the 2-site of the ribose group, such as e.g. —F, —NH$_2$, —CH$_3$, especially CH$_3$. Of course, —OH and SH groups are excluded for the I-ODNs according to the present invention to be present on the 2'-site of the ribose, especially the ribose residue for the inosine NMP.

The length of the ODNs according to the present invention is in the range of the standard ODNs used according to the prior art. Therefore molecules with a total length under 4 and above 150 show gradually decreasing immunostimulatory potential. Preferred ODNs contain between 10 and 60, especially between 15 and 40 bases (nucleosides), implying that a+b in formula I is between 10 and 60, preferably between 15 and 40 in these preferred embodiments.

Whereas the ribonucleic acid molecules containing inosine and cytidine described to be immunostimulatory in the prior art have been large and relatively undefined polynucleic acids with molecular weights far above 200,000 (a commercially available polyinosinic-polycytidylic acid from Sigma Chemicals has a molecular weight ranging from 220,000 to 460,000 (at least 500-1000 C+I residues). The molecules according to the present invention are DNA molecules of much shorter length with a well defined length and composition, being highly reproducible in products.

It is further preferred that the deoxyinosine containing NMP of the I-ODNs according to formula I is a monothiophosphate with one to four sulfur atoms and that also further NMPs, especially all further NMPs, are present as nucleoside monothiophosphates, because such ODNs display higher nuclease resistance (it is clear for the present invention that the "mono" in the "monothiophosphates" relates to the phosphate, i.e. that one phosphate group (one phosphor atom) is present in each NMP). Preferably, at least one of $X_1$ and $X_2$ is S and at least one of $X_3$ and $X_4$ is O in the NMPs according to the present invention. Preferably, $X_3$ and $X_4$ are O. ($X_3$ may be (due to synthesis of the NMP) derived e.g. from the phosphate group or from the 3'-group of the NMP-ribose).

Preferably the ODNs according to the present invention contain the sequence

```
                                        (SEQ ID NO: 28)
       hhh wdi dhh h, (SEQ ID NO: 10)
       nhh hhh wdi nhh hhh hhh wn, (SEQ ID NO: 11)
       nhh wdi din hhh hdi ndi nh, (SEQ ID NO: 12)
       nhh hhh wdi dhh hhh hhh wn
       or
                                        (SEQ ID NO: 13)
       nhh wdi did hhh hdi ddi dh,
``` wherein
any n is a 2'-deoxynucleoside monophosphate or monothiophosphate, selected from the group consisting of deoxyadenosine-, deoxyguanosine-, deoxycytosine- or deoxythymidine-monophosphate or -monothiophosphate,
any h is a 2'-deoxynucleoside monophosphate or monothiophosphate, selected from the group consisting of deoxyadenosine-, deoxycytosine- or deoxythymidine-monophosphate or monothiophosphate
i is deoxyinosine-monophosphate or -monothiophosphate,
any w is a 2'-deoxynucleoside monophosphate or monothiophosphate, selected from the group consisting of deoxyadenosine- or deoxythymidine-monophosphate or -monothiophosphate, and any d is a 2'-deoxynucleoside monophosphate or monothiophosphate, selected from the group consisting of deoxyadenosine-, deoxyguanosine- or deoxythymidine-monophosphate or monothiophosphate.

As outlined above, a specific motif (such as CpG or a palindrome) is not necessary for the I-ODNs according to the present invention. However, ODNs containing a CI motif are preferred so that in a preferred embodiment the ODN according to formula I contains
at least one 2' deoxycytosine-monophosphate or -monothiophosphate 3'-adjacent to a 2'-deoxyinosinemonophosphate or -monothiophosphate to form such a 5'-CI 3'-motif.

Preferred ODNs according to the present invention contain one or more of the sequence

```
                                        (SEQ ID NO: 1)
       gacitt, (SEQ ID NO: 2)
       iacitt, (SEQ ID NO: 3)
       gaictt, (SEQ ID NO: 4)
       iaictt,
``` wherein
a is deoxyadenosine-monophosphate or -monothiophosphate,
g is deoxyguanosine-monophosphate or -monothiophosphate,
i is deoxyinosine-monophosphate or -monothiophosphate,
c is deoxycytosine-monophosphate or -monothiophosphate and
t is deoxythymidine-monophosphate or -monothiophosphate.

The I-ODNs according to the present invention are especially suitable for application in the pharmaceutical field, e.g. to be applied as a medicine to an animal or to humans. They are specifically adapted to act as an immunostimulatory agent, especially in or together with vaccine compositions.

Therefore, the present invention also relates to a pharmaceutical composition comprising an ODN according to the present invention.

Since a preferred pharmaceutical composition according to the present invention is a vaccine, this composition should contain an antigen besides the ODN according to the present invention. The potential of this antigen to raise a protection/immune response of the vaccinated individual is strongly increased by combining it with the ODNs according to the present invention, especially due to their immunostimulatory activity.

A vaccine can contain a whole variety of different antigens. Examples of antigens are whole-killed organisms such as inactivated viruses or bacteria, fungi, protozoa or even cancer cells. Antigens may also consist of subfractions of these or organisms/tissues, of proteins, or, in their most simple form, of peptides. Antigens can also be recognised by the immune system in form of glycosylated proteins or peptides and may also be or contain polysaccharides or lipids. Short peptides can be used since for example cytotoxic T cells (CTL) recognize antigens in form of short usually 8-11 amino acids long peptides in conjunction with major histocompatibility complex (MHC) (Rammensee et al., Immunogenetics 41, (1995), 178-228). B cells recognize longer peptides starting at around 15 amino acids (Harrow et al, Cold Spring Harbor: Cold Spring Harbor Laboratory, (1988)). By contrast to T cell epitopes, the three dimensional structure of B cell antigens may also be important for recognition by antibodies. In order to obtain sustained, antigen-specific immune responses, adjuvants are helpful to trigger immune cascades that involve all cells of the immune system necessary. Primarily, adjuvants are acting, but are not restricted in their mode of action, on so-called antigen presenting cells (APCs). These cells usually first encounter the antigen(s) followed by presentation of processed or unmodified antigen to immune effector. Intermediate cell types may also be involved. Only effector cells with the appropriate specificity are activated in a productive immune response. The adjuvant may also locally retain antigens and co-injected other factors. In addition the adjuvant may act as a chemoattractant for other immune cells or may act locally and/or systemically as a stimulating agent for the immune system.

According to a preferred embodiment, T cell epitopes are used as antigens. Alternatively, a combination of T cell epitopes and B cell epitopes may also be preferred.

The antigens to be used in the present compositions are not critical. Also mixtures of different antigens are of course possible to be used according to the present invention. Preferably, proteins or peptides derived from a viral or a bacterial pathogen or from fungi or parasites are used as such antigens (including derivatized antigens or glycosylated or lipidated antigens or polysaccharides or lipids). Another preferred source of antigens are tumor antigens. Preferred pathogens are selected from human immunodeficiency virus (HIV), hepatitis A and B viruses, hepatitis C virus (HCV), Rous sarcoma virus (RSV), Epstein Barr virus (EBV) Influenza virus, Rotavirus, *Staphylococcus aureus, Chlamydia pneumonias, Chlamydia trachomatis, Mycobacterium tuberculosis, Streptococcus pneumonias, Bacillus anthracis, Vibrio cholerae, Plasmodium* sp. (*Pl. falciparum, Pl. vivax*, etc.), *Aspergillus* sp. or *Candida albicans*. Antigens may also be molecules expressed by cancer cells (tumor antigens). The derivation process may include the purification of a specific protein from the pathogen/cancer cells, the inactivation of the pathogen as well as the proteolytic or chemical derivatization or stabilisation of such a protein. In the same way also tumor antigens (cancer vaccines) or autoimmune antigens may be used in the pharmaceutical composition according to the present invention. With such compositions a tumor vaccination or a treatment for autoimmune diseases may be performed.

In the case of peptide antigens the use of peptide mimitopes/agonists/superagonists/antagonists or peptides changed in certain positions without affecting the immunologic properties or non-peptide mimitopes/agonists/superagonists/antagonists (reviewed in Sparbier and Walden, 1999) is included in the current invention. Peptide antigens may also contain elongations either at the carboxy or at the amino terminus of the peptide facilitating interaction with the polycationic compound(s) or the immunostimulatory compound(s). For the treatment of autoimmune diseases peptide antagonists may be applied.

Antigens may also be derivatized to include molecules enhancing antigen presentation and targeting of antigens to antigen presenting cells.

In one embodiment of the invention the pharmaceutical composition serves to confer tolerance to proteins or protein fragments and peptides which are involved in autoimmune diseases. Antigens used in this embodiments serve to tolerize the immune system or downregulate immune responses against epitopes involved in autoimmune processes.

Preferably the pharmaceutical composition according to the present invention, especially in the form of a vaccine, further comprises a polycationic polymer, preferably a polycationic peptide, especially polyarginine, polylysine or an antimicrobial peptide.

The polycationic compound(s) to be used according to the present invention may be any polycationic compound which shows the characteristic effect according to the WO 97/30721. Preferred polycationic compounds are selected from basic polypeptides, organic polycations, basic polyaminoacids or mixtures thereof. These polyaminoacids should have a chain length of at least 4 amino acid residues (see: Tuftsin as described in Goldman et al (1983)). Especially preferred are substances containing peptidic bounds, like polylysine, polyarginine and polypeptides containing more than 20%, especially more than 50% of basic amino acids in a range of more than 8, especially more than 20, amino acid residues or mixtures thereof. Other preferred polycations and their pharmaceutical compositions are described in WO 97/30721 (e.g. polyethyleneimine) and WO 99/38528. Preferably these polypeptides contain between 20 and 500 amino acid residues, especially between 30 and 200 residues.

These polycationic compounds may be produced chemically or recombinantly or may be derived from natural sources.

Cationic (poly)peptides may also be polycationic anti-bacterial microbial peptides with properties as reviewed in (Ganz and Lehrer, 1999; Hancock, 1999). These (poly)peptides may be of prokaryotic or animal or plant origin or may be produced chemically or recombinantly (Andreu and Rivas, 1998; Ganz and Lehrer, 1999; Simmaco et al., 1998). Peptides may also belong to the class of defensins (Ganz, 1999; Ganz and Lehrer, 1999).

Such host defense peptides or defensives are also a preferred form of the polycationic polymer according to the present invention. Generally, a compound allowing as an end product activation (or down-regulation) of the adaptive immune system, preferably mediated by APCs (including dendritic cells) is used as polycationic polymer.

Especially preferred for use as polycationic substance in the present invention are cathelicidin derived antimicrobial peptides or derivatives thereof (A 1416/2000, incorporated herein by reference), especially antimicrobial peptides derived from mammal cathelicidin, preferably from human, bovine or mouse, or neuroactive compounds, such as (human) growth hormone.

Polycationic compounds derived from natural sources include HIV-REV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelin. For example, mouse cathelin is a peptide which has the amino acid sequence NH$_2$-RLAGLL-RKGGEKIGEKLKKIGOKIKNFFQKLVPQPE-COOH (SEQ ID NO:5). Related or derived cathelin substances contain the whole or parts of the cathelin sequence with at least 15-20 amino acid residues. Derivations may include the substitution or modification of the natural amino acids by amino acids which are not among the 20 standard amino acids. Moreover, further cationic residues may be introduced into such cathelin molecules. These cathelin molecules are preferred to be combined with the antigen and the immunogenic ODN according to the present invention. However, these cathelin molecules surprisingly have turned out to be also effective as an adjuvant for a antigen without the addition of further adjuvants. It is therefore possible to use such cathelin molecules as efficient adjuvants in vaccine formulations with or without further immunactivating substances.

Another preferred polycationic substance to be used according to the present invention is a synthetic peptide containing at least 2 KLK-motifs separated by a linker of 3 to 7 hydrophobic amino acids (A 1789/2000, incorporated herein by reference).

It was very surprising that the immunostimulating effect of the pharmaceutical composition according to the present invention was significantly higher than it could be expected from the addition of the effects of each single component or even the addition of the effects of the ODN or the polycation with the antigen.

B and E in formula I are common groups for 5' and/or 3' ends of nucleic acid molecules. Examples for such groups are readily available for the skilled man in the art (see e.g. "Oligonucleotides and Analogues—A Practical Approach" (1991), ed. Eckstein, Oxford University Press). For the I-ODNs according to the present invention B and/or E are preferably selected independently from —H, —$CH_3$, —$COCH_3$, —OH, —CHO, a phosphate, thiophosphate, sulfate or a thiosulfate group, or a phosphoalkylgroup, especially with an alkyl length of $C_1$-$C_6$ and/or with a terminal amino group (the amino group may e.g. be used for further labelling of the I-ODNs according to the present invention, e.g. —$PO_4$—$(CH_2)_n$—$NH_2$ or —$PO_4$—$(CH_2)_n$—NH-Label). Especially preferred as B are nucleosides, especially the 2' deoxynucleotides mentioned above (i.e. without the phosphate or thiophosphate group). Alternatively these groups may also contain linker groups to other molecules, especially carrier molecules or labels. In such forms of ODNs wherein the ODNs are bound to solid surfaces or particles or labels, these surfaces, particles, labels, etc. are then also part of the B and/or E groups.

Of course, any ionised (salt) form or tautomeric forms of the molecules according to formula I are included in this formula I.

The pharmaceutical composition according to the present invention may further comprise further active ingredients (pharmaceutically active substances), especially substances which are usable in a vaccine connection. Preferred embodiments of such further active ingredients are cytokines, anti-inflammatory substances, antimicrobial substances or combinations thereof.

Of course, the pharmaceutical composition according to the present invention may further contain auxiliary substances, especially a pharmaceutically acceptable carrier, buffer substances, stabilizers or combinations thereof.

The relative amounts of the ingredients in the present pharmaceutical composition are highly dependent on the necessities of the individual antigen and on the animal/human to which this composition should be applied to. Therefore, the pharmaceutical composition according to the present invention preferably contains one or more ODNs according to the present invention, preferably 1 pg to 10 g, preferably 1 ng to 1 g, more preferred 100 ng to 10 mg, especially 10 mg to 1 mg. The antigen as well as the polycationic polymer may be applied in similar dosages, a range of 1 to 10,000 mg antigen and 0.1 to 1,000 mg polycation per vaccination is preferred.

The present compositions may be applied to a patient, e.g. a vaccination candidate, in efficient amounts e.g. by weekly, bi-weekly or monthly intervals. Patients to be treated with the present compositions may also be vaccinated repeatedly or only once. A preferred use of the present invention is the active immunisation, especially of humans or animals without protection against the specific antigen.

The route of application for the present composition is not critical, e.g. subcutaneous, intramuscular, intradermal or transdermal injection is suitable as well as oral uptake.

It is also possible to apply the present composition separately e.g. by injecting the immunostimulating substance separately from the antigen/polycation composition. The present invention is therefore also directed to a kit comprising a composition containing the antigen and the polycationic polymer as one component and a composition containing the immunostimulating or chemotactic substance as a second component.

The components may be applied at the same site or time, however, an application at different sites or at a different time or for a different time period is also possible. It is also possible to vary the systemic or local applications of the composition or the components, respectively.

Details of the present invention are described by the following examples and the figures, but the invention is of course not limited thereto.

FIG. 1 shows the immune response against the ovalbumin-derived peptide $OVA_{257-264}$ after the injection of $OVA_{257-264}$, poly-L-arginine (pR 60) and deoxyinosine I-containing oligodeoxynucleotides (I-ODN) or CpG 1668. Mice were injected into the hind footpads with mixtures as indicated. Four days later draining lymph node cells were ex vivo stimulated with $OVA_{257-264}$. The number of IFN-g-producing cells was determined 24 hours later using an ELISPOT assay. Results are expressed as the number of spots/$1 \times 10^6$ lymph node cells.

FIG. 2 shows the induction of systemic TNF-a production after the injection of $OVA_{257-264}$, poly-L-arginine (pR 60) and I-containing oligodeoxynucleotides (I-ODN) or CpG 1668. Mice were injected into the hind footpads with mixtures as indicated. One hour after injection blood was taken from the tail vein and serum was prepared. The concentration of TNF-a in the sera was determined using an ELISA.

FIG. 3 shows the immune response against the Ovalbumin-derived peptide $OVA_{257-264}$ after the injection of $OVA_{257-264}$, poly-L-arginine (pR60) and deoxyinosine-containing oligodeoxynucleotides (I-ODN), CpG 1668 or GpC. Mice were injected into the hind footpads with mixtures as indicated. Four days later, draining lymph node cells were ex vivo stimulated with $OVA_{257-264}$, an irrelevant peptide $mTRP2_{181-188}$ (murine tyrosinase related protein-2, VYDFFVWL (SEQ ID NO: 8)) or pR 60. The number of IFN-g producing cells was determined 24 hours later using an ELISPOT assay. Results are expressed as the number of spots/$1 \times 10^6$ lymph node cells with standard deviation of triplicates.

FIG. 4 shows the induction of systemic TNF-a production after the injection of $OVA_{257-264}$, poly-L-arginine (pR 60) and I-containing oligodeoxynucleotides (I-ODN), GpC or CpG 1668. Mice were injected into the hind footpads with mixtures as indicated. One hour after injection blood was taken from the tail vein and serum was prepared. The concentration of TNF-a and IL-6 in the sera was determined using cytokine-specific ELISAs.

FIG. 5 shows the immune response against the Ovalbumin-derived peptide $OVA_{257-264}$ after the injection of TRP-2, poly-L-arginine, CpG 1668 or random 20-mer sequences containing deoxyinosine. Mice were injected into the hind footpads with mixtures as indicated. Four days later, draining lymph node cells were ex vivo stimulated with TRP-2, an irrelevant peptide OVA$_{257-264}$ or pR 60. The number of IFN-g producing cells was determined 24 hours later using an ELISPOT assay. Results are expressed as the number of spots/$1 \times 10^6$ lymph node cells with standard deviation of triplicates.

Figure 9:
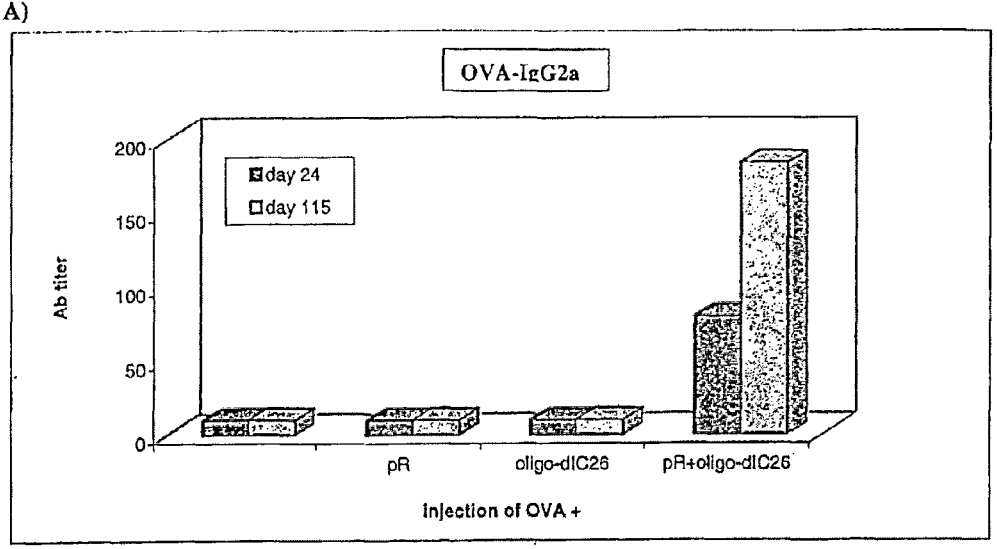
Figure 9:
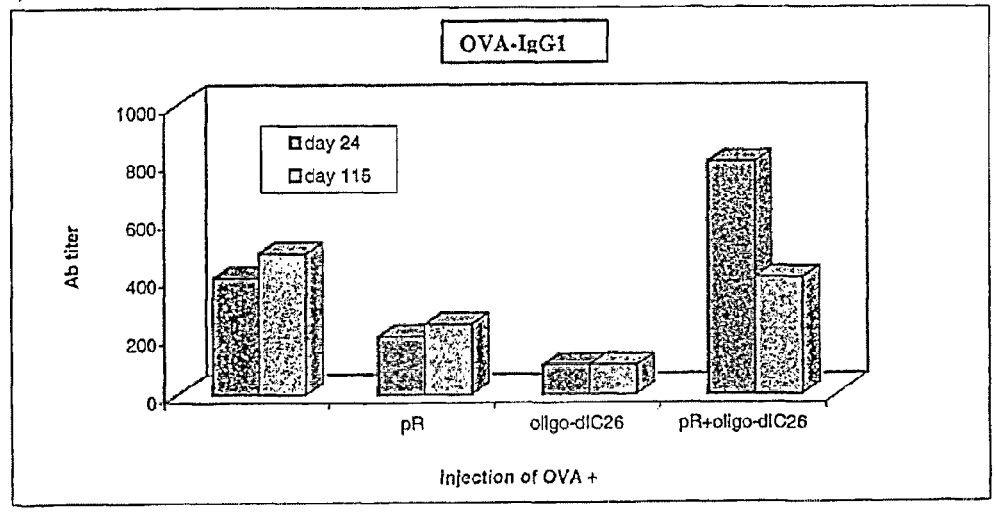

FIG. 9 shows that the combined application of ovalbumin (OVA) with oligo-dIC$_{26-mer}$ and pR enhances production of OVA-specific IgG antibodies. Mice were injected subcutaneously into the footpad with mixtures as indicated. At day 24 and 115 after injection, sera were collected and screened by ELISA for OVA-specific IgG2a (A) and IgG1 (B) antibodies. The results are shown as the antibody titer.

EXAMPLES

In all experiments thiophosphate-substituted ODNs (with thiophosphate residues substituting for phosphate, hereafter called "thiophosphate substituted oligodeoxynucleotides") were used since such ODNs display higher nuclease resistance (Ballas et al., 1996; Krieg et al., 1995; Parronchi et al., 1999).

Example 1

The Combined Injection of Different I-ODNs and Poly-L-Arginine (pR 60) Synergistically Enhances the Immune Response Against an Ovalbumin-Derived Peptide

| | |
|---|---|
| Mice | C57Bl/6 (Harlan/Olac) |
| Peptide | OVA$_{257-264}$-Peptide (SIINFEKL) (SEQ ID NO: 6), a MHC class I (H-2Kb)-restricted epitope of chicken ovalbumin (Rotzschke et al., 1991), was synthesized using standard solid phase F-moc chemistry synthesis, HPLC purified and analysed by mass spectroscopy for purity. Dose: 300 mg/mouse |
| Poly-L-arginine60 (pR60) | Poly-L-arginine with an average degree of polymerization of 60 arginine residues; SIGMA chemicals Dose: 100 mg/mouse |
| CpG-ODN 1668 | thiophosphate substituted ODNs containing a CpG motif: tcc at<u>g acg t</u>tc ctg atg ct (SEQ ID NO: 7), were synthesized by NAPS GmbH, Göttingen. Dose: 5 nmol/mouse |
| I-ODN 1 | thiophosphate substituted ODNs containing deoxyinosine: tcc ati aci ttc ctg atg ct (SEQ ID NO: 14), were synthesized by NAPS GmbH, Göttingen. Dose: 5 nmol/mouse |
| I-ODN 2 | thiophosphate substituted ODNs containing deoxyinosine: tcc atg aci ttc ctg atg ct (SEQ ID NO: 15), were synthesized by NAPS GmbH, Göttingen. Dose: 5 nmol/mouse |
| I-ODN 3 | thiophosphate substituted ODNs containing deoxyinosine: tcc ati aci ttc cti ati ct (SEQ ID NO: 16), were synthesized by NAPS GmbH, Göttingen. Dose: 5 nmol/mouse |

Experimental Groups (5 Mice Per Group)
1. OVA$_{257-264}$
2. OVA$_{257-264}$+pR 60
3. OVA$_{257-264}$+CpG 1668
4. OVA$_{257-264}$+I-ODN 1
5. OVA$_{257-264}$+I-ODN 2
6. OVA$_{257-264}$+I-ODN 3
7. OVA$_{257-264}$+CpG 1668+pR 60
8. OVA$_{257-264}$+I-ODN 1+pR 60
9. OVA$_{257-264}$+I-ODN 2+pR 60
10. OVA$_{257-264}$+I-ODN 3+pR 60

Figure 1:
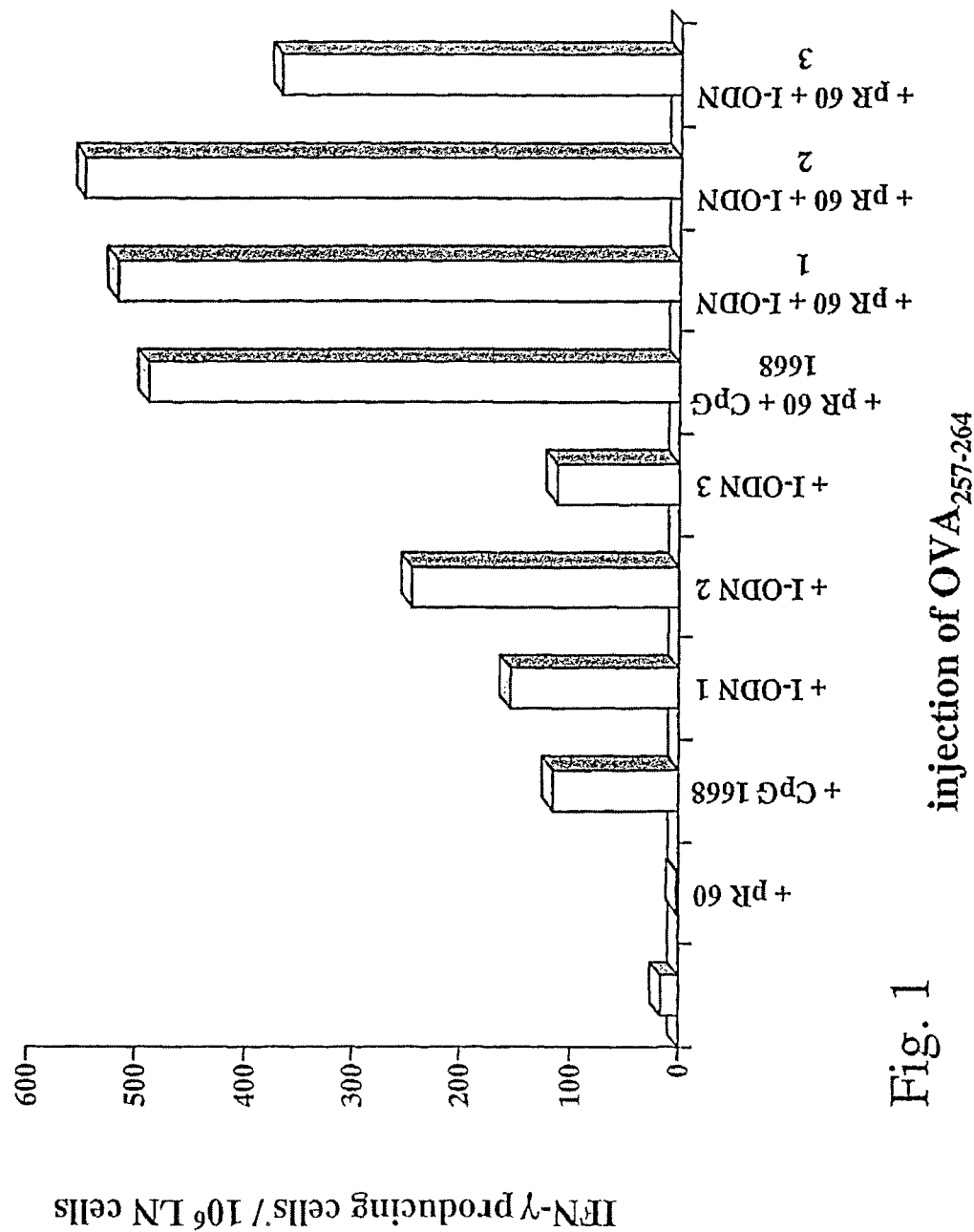

On day 0 mice were injected into each hind footpad with a total volume of 100 ml (50 ml per footpad) containing the above mentioned compounds. Animals were sacrificed 4 days after injection and popliteal lymph nodes were harvested. Lymph nodes were passed through a 70 mm cell strainer and washed twice with DMEM medium (GIBCO BRL) containing 5% fetal calf serum (FCS, SIGMA chemicals). Cells were adjusted to $3 \times 10^6$ cells/ml in DMEM/5%/FCS. An IFN-g ELISPOT assay was carried out in triplicates as described (Miyahira et al., 1995). This method is a widely used procedure allowing the quantification of antigen-specific T cells. Lymphocytes were stimulated ex vivo with medium background-control, OVA$_{257-264}$-peptide or Concanavalin A (Con A). Spots representing single IFN-g producing T cells were counted and the number of background spots was subtracted from all samples. The high number of spots detected after the stimulation with Con A (data not shown) indicate a good condition of the used lymphocytes. For each experimental group of mice the number of spots/$1 \times 10^6$ cells are illustrated in FIG. 1.

Figure 2:
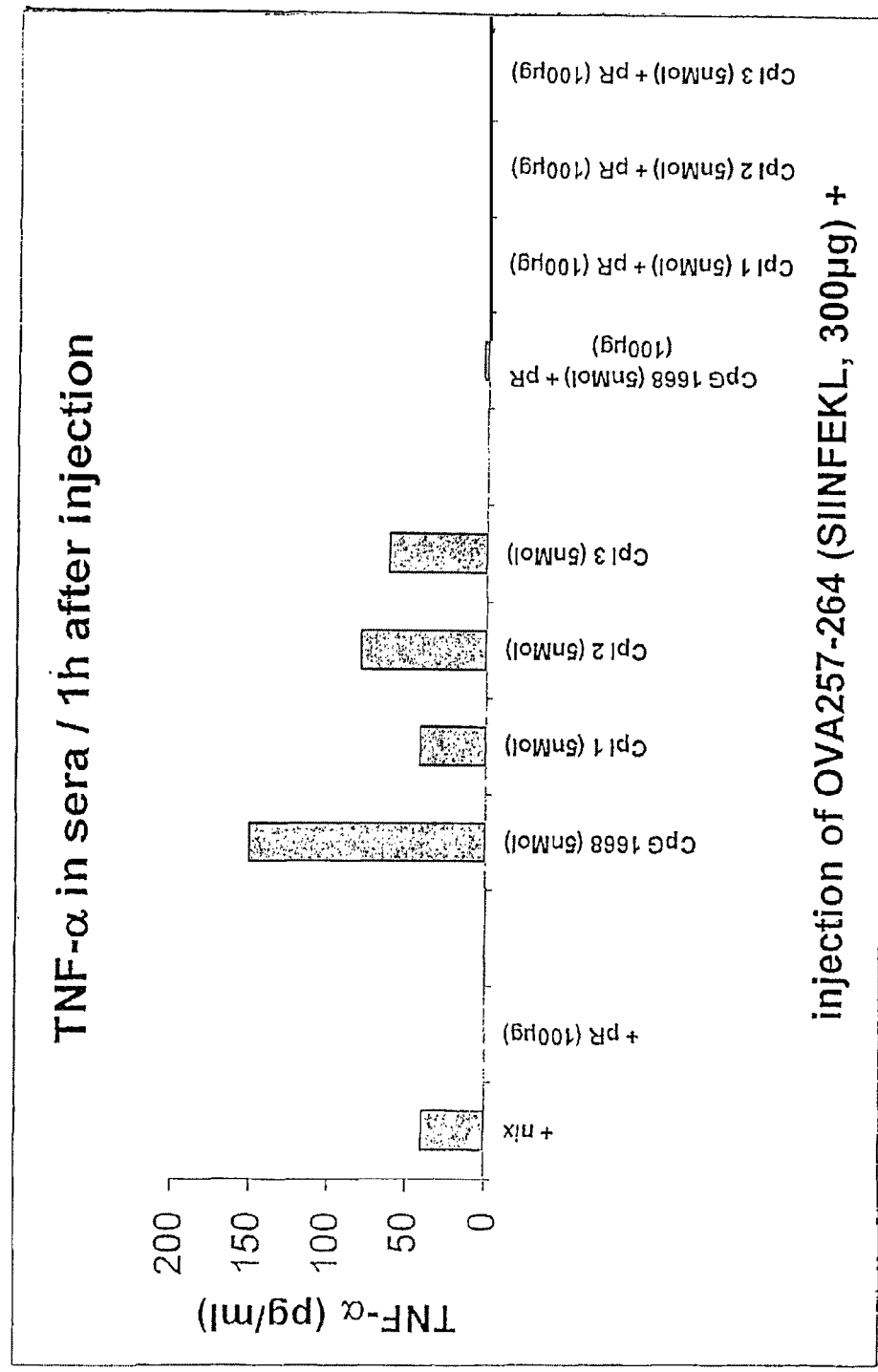

One hour after injection blood was taken from the tail vein and serum was prepared to determine the induction of systemic TNF-a using an ELISA (FIG. 2).

Example 2

The Exchange of Guanosine by Desoxy-Inosine Converts the Non-Immunogeneic GpC-Sequence to a Highly Immunogeneic One, Especially when Combined with Poly-L-Arginine (pR60)

| | |
|---|---|
| Mice | C57B1/6 (Harlan/Olac) |
| Peptide class I | OVA$_{257-264}$-Peptide (SIINFEKL (SEQ ID NO: 6)), a MHC (H-2Kb)-restricted epitope of chicken ovalbumin (Rotzschke et al., 1991), was synthesized using standard solid phase F-moc synthesis, HPLC purified and analysed by mass spectroscopy for purity. Dose: 300 µg/mouse |
| Poly-L-arginine 60 (pR60) | Poly-L-arginine with an average degree of polymerization of 60 arginine residues; SIGMA chemicals Dose: 100 µg/mouse |

| | |
|---|---|
| CpG-ODN 1668 | thiophosphate substituted ODNs containing a CpG motif: tcc atg acg ttc ctg atg ct (SEQ ID NO: 7), were synthesized by NAPS GmbH, Göttingen. Dose: 5 nmol/mouse |
| GpC-ODN | thiophosphate substituted ODNs containing an non-immunogeneic GpC motif: tcc atg agc ttc ctg atg ct (SEQ ID NO: 17) were synthesized by NAPS GmbH, Göttingen. Dose: 5 nmol/mouse |
| I-ODN 9 | thiophosphate substituted ODNs containing deoxyinosine: tcc atg aic ttc ctg atg ct (SEQ ID NO: 18) were synthesized by NAPS GmbH, Göttingen. Dose: 5 nmol/mouse |
| I-ODN 10 | thiophosphate substituted ODNs containing deoxyinosine: tcc ati aic ttc cti ati ct (SEQ ID NO: 19) were synthesized by NAPS GmbH, Göttingen. Dose: 5 nmol/mouse |

Experimental Groups (5 Mice Per Group)

$OVA_{257-264}$ $OVA_{257-264}$+pR 60

$OVA_{257-264}$+CpG 1668

$OVA_{257-264}$+GpC $OVA_{257-264}$+I-ODN 9

$OVA_{257-264}$+I-ODN 10

$OVA_{257-264}$+CpG 1668+pR 60

$OVA_{257-264}$+GpC+pR 60

$OVA_{257-264}$+I-ODN 9+pR 60

$OVA_{257-264}$+I-ODN 10+pR 60

Figure 3:
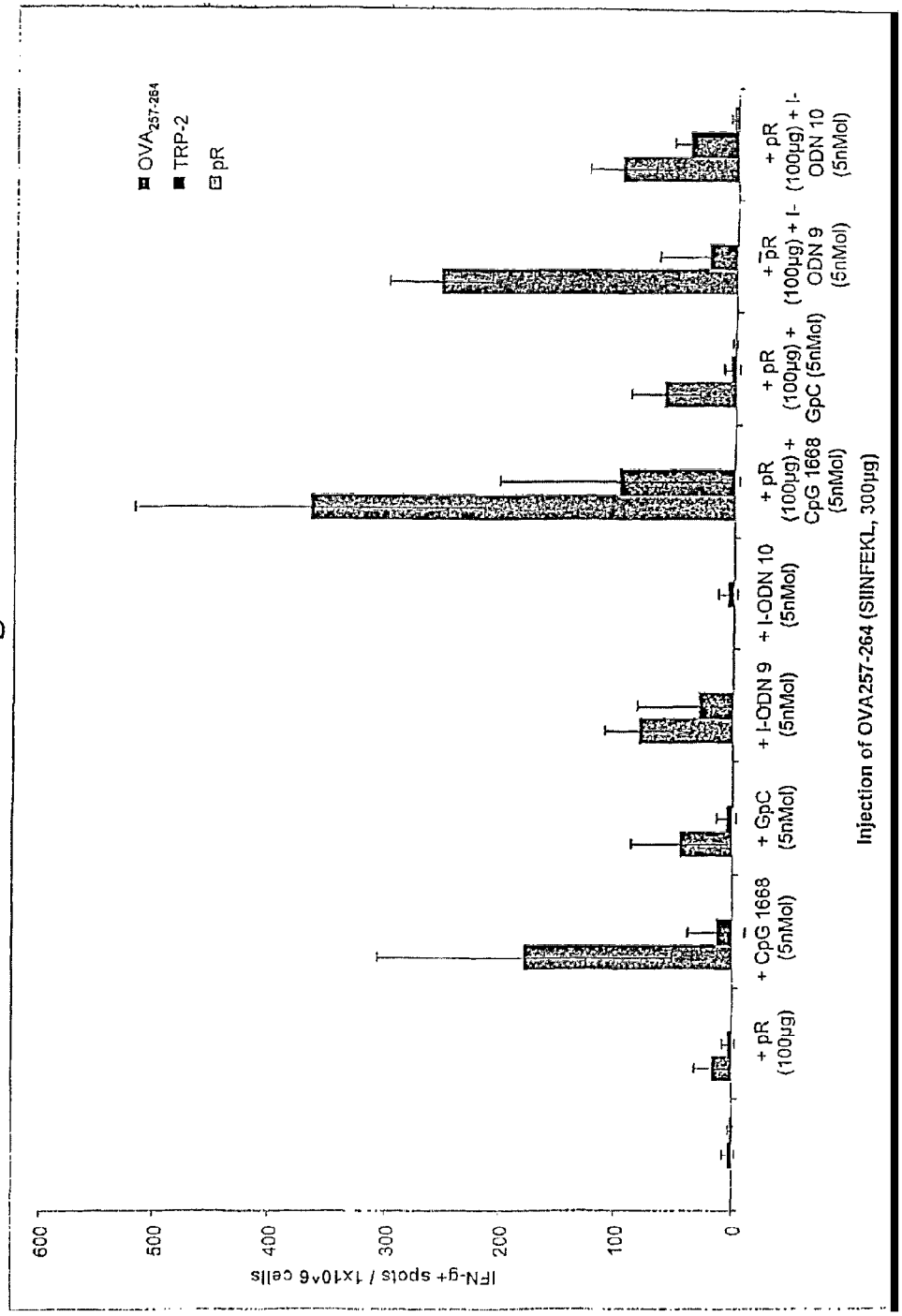
Figure 4:
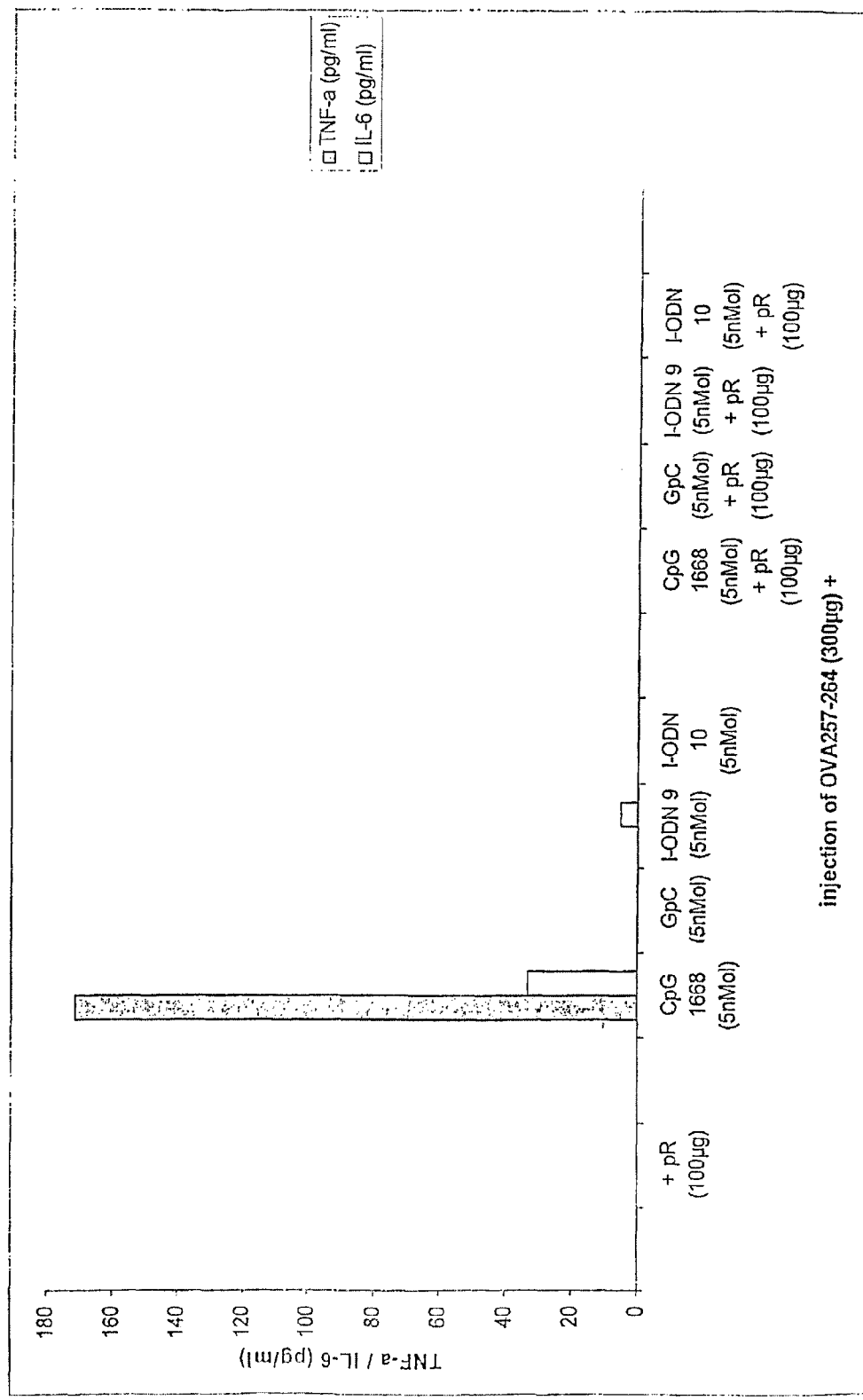

On day 0 mice were injected into each hind footpad with a total volume of 100 µl (50 µl per footpad) containing the above mentioned compounds. Animals were sacrificed 4 days after injection and popliteal lymph nodes were harvested. Lymph nodes were passed through a 70 µm cell strainer and washed twice with DMEM medium (GIBCO BRL) containing 5% fetal calf serum (FCS, SIGMA chemicals). Cells were adjusted to $3\times10^6$ cells/ml in DMEM/5% FCS. An IFN-g ELISPOT assay was carried out in triplicates as described (Miyahira et al., 1995). This method is a widely used procedure allowing the quantification of antigen-specific T cells. Lymphocytes were stimulated ex vivo in triplicates with medium (background), $OVA_{257-264}$-peptide, an irrelevant peptide $mTRP-2_{181-188}$ (murine tyrosinase related protein-2, VYDFFVWL (SEQ ID NO:8)), pR 60 and Concanavalin A (Con A). Spots representing single IFN-g producing T cells were counted and the number of background spots was subtracted from all samples. The high number of spots detected after the stimulation with Con A (data not shown) indicate a good condition of the used lymphocytes. For each experimental group of mice the number of spots/$1\times10^6$ cells are illustrated in FIG. 3, the standard deviation of ex vivo-stimulated triplicates are given. One hour after injection blood was taken from the tail vein and serum was prepared to determine the induction of systemic TNF-a and IL-6 using cytokine-specific ELISAs (FIG. 4).

Example 3

The Combined Injection of Random 20-Mer Sequences Containing Deoxyinosine and a Melanoma-Derived Peptide Induces a Strong Immune Response Against the Peptide which can be Further Enhanced by the Co-Application of Poly-L-Arginine (pR 60)

| | |
|---|---|
| Mice | C57B1/6 (Harlan/Olac) |
| Peptide | TRP-2-peptide (VYDFFVWL (SEQ ID NO: 8), a MHC class I ($H-2K^b$)-restricted epitope of mouse tyrosinase related protein-2 (Bloom et al., 1997) was synthesized by standard solid phase F-moc synthesis, HPLC purified and analyzed by mass spectroscopy for purity. Dose: 300 µg/mouse |
| Poly-L-arginine 60 (pR60) | Poly-L-arginine with an average degree of polymerization of 60 arginine residues; SIGMA chemicals Dose: 100 µg/mouse |
| CpG-ODN 1668 | thiophosphate substituted ODNs containing a CpG motif: tcc atg acg ttc ctg atg ct (SEQ ID NO: 7), were synthesized by NAPS GmbH, Göttingen. Dose: 5 nmol/mouse |
| Wdi thiophosphate substituted ODNs: | nhh hhh wdi nhh hhh hhh wn (SEQ ID NO: 10) were synthesized by NAPS GmbH, Göttingen. Dose: 5 nmol/mouse |
| Wdidin thiophosphate substituted ODNs: | nhh hhh wdi nhh hhh hhh wn (SEQ ID NO: 10) were synthesized by NAPS GmbH, Göttingen. Dose: 5 nmol/mouse |
| Wdid thiophosphate substituted ODNs: | nhh hhh wdi dhh hhh hhh wn (SEQ ID NO: 12) were synthesized by NAPS GmbH, Göttingen. Dose: 5 nmol/mouse |
| Wdidid thiophosphate substituted ODNs: | nhh wdi did hhh hdi ddi dh (SEQ ID NO: 13) were synthesized by NAPS GmbH, Göttingen. Dose: 5 nmol/mouse |

Experimental Groups (5 Mice Per Group)
1. TRP-2
2. TRP-2+pR 60
3. TRP-2+CpG 1668
4. TRP-2+wdi
5. TRP-2+wdidin
6. TRP-2+wdid
7. TRP-2+wdidid
8. TRP-2+CpG 1668+pR 60
9. TRP-2+wdi+pR 60
10. TRP-2+wdidin+pR 60
11. TRP-2+wdid+pR 60
12. TRP-2+wdidid+pR 60

On day 0 mice were injected into each hind footpad with a total volume of 100 µl (50 µl per footpad) containing the above mentioned compounds. Animals were sacrificed 4 days after injection and popliteal lymph nodes were harvested. Lymph nodes were passed through a 70 µm cell strainer and washed twice with DMEM medium (GIBCO BRL) containing 5% fetal calf serum (FCS, SIGMA chemicals). Cells were adjusted to $3\times10^6$ cells/ml in DMEM/5% FCS. An IFN-g ELISPOT assay was carried out in triplicates as described (Miyahira et al., 1995). This method is a widely used procedure allowing the quantification of antigen-specific T cells.

Figure 5:
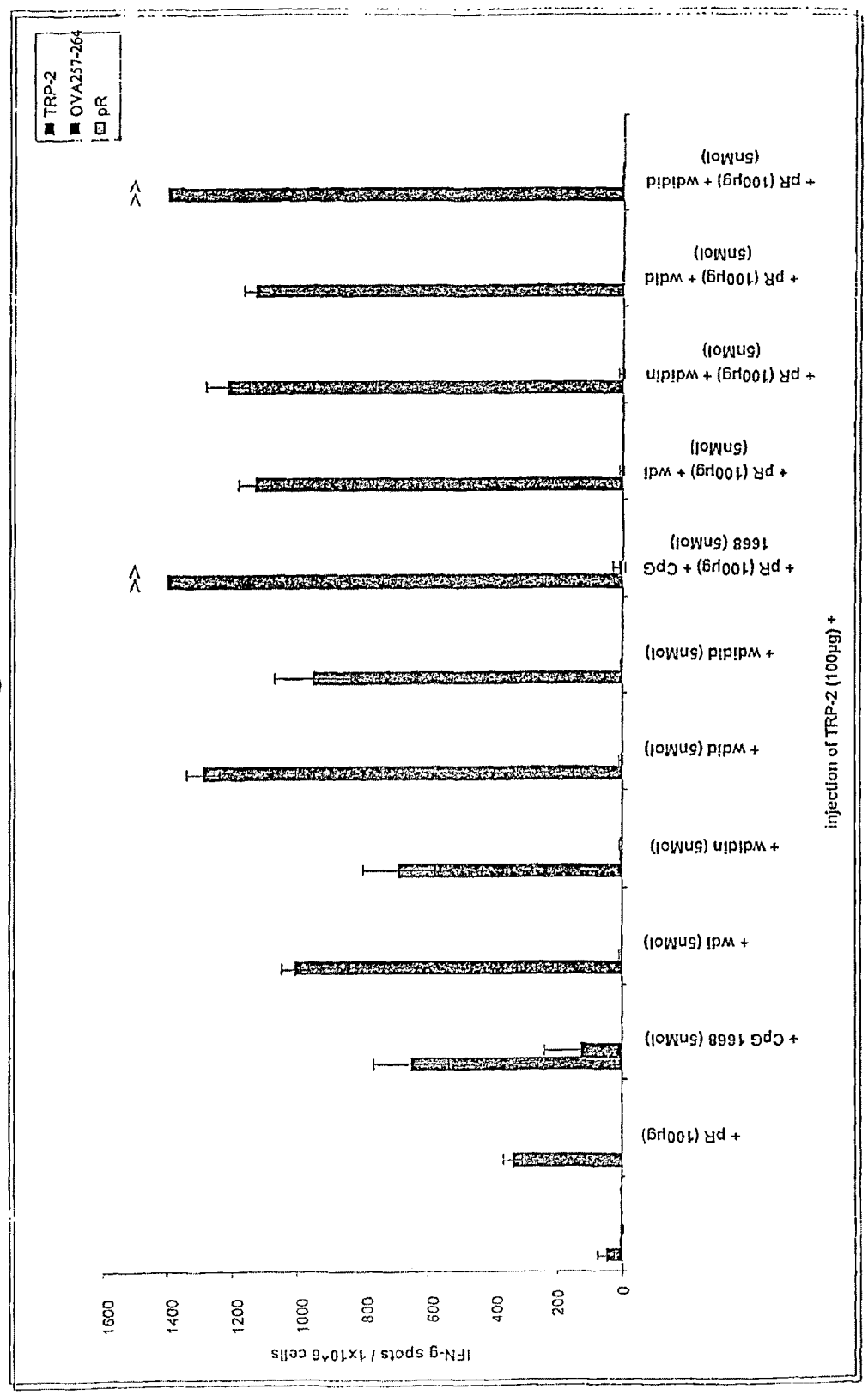

Lymphocytes were stimulated ex vivo in triplicates with medium (background), TRP-2-peptide, an irrelevant OVA$_{257-264}$-peptide, pR 60 and Concanavalin A (Con A). Spots representing single IFN-g producing T cells were counted and the number of background spots was subtracted from all samples. The high number of spots detected after the stimulation with Con A (data not shown) indicate a good condition of the used lymphocytes. For each experimental group of mice the number of spots/1×10$^6$ cells are illustrated in FIG. 5, the standard deviation of ex vivo-stimulated triplicates are given.

Example 4

The Combined Injection of I-ODN and Poly-L-Arginine (pR 60) Synergistically Enhances the Immune Response Against a Melanoma-Derived Peptide Experimental Groups (5 Mice Per Group)
1. TRP-2$_{181-188}$
2. TRP-2$_{181-188}$+pR 60
3. TRP-2$_{181-188}$+CpG 1668
4. TRP-2$_{181-188}$+I-ODN 2
5. TRP-2$_{181-188}$+CpG 1668+pR 60
6. TRP-2$_{181-188}$+I-ODN 2+pR 60

Figure 6:
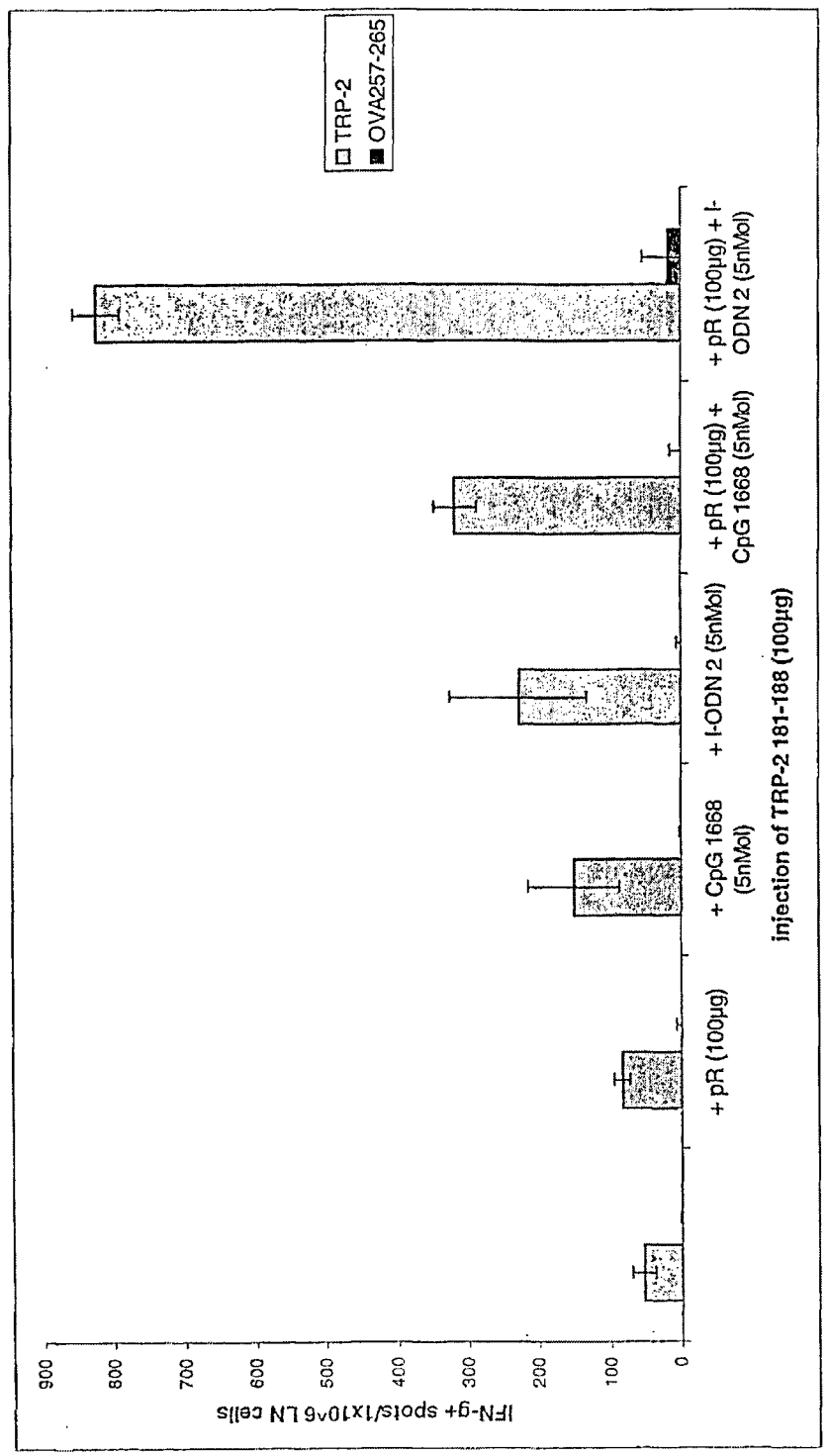
FIG. 6 shows the combined injection of I-ODN and poly-L-arginine (pR 60) together with a Melanoma-derived peptide.

On day 0 mice were injected into each hind footpad with a total volume of 100 µl (50 µl per footpad) containing the above mentioned compounds. Animals were sacrificed 4 days after injection and popliteal lymph nodes were harvested. Lymph nodes were passed through a 70 µm cell strainer and washed twice with DMEM medium (GIBCO BRL) containing 5% fetal calf serum (FCS, SIGMA chemicals). Cells were adjusted to 3×10$^6$ cells/ml in DMEM/5%/FCS. An IFN-γ ELISPOT assay was carried out in triplicates as described (Miyahira et al., 1995). This method is a widely used procedure allowing the quantification of antigen-specific T cells. Lymphocytes were stimulated ex vivo in triplicates with medium background-control, TRP-2$_{181-188}$-peptide, an irrelevant OVA$_{257-264}$-peptide and Concanavalin A (Con A). Spots representing single IFN-γ producing T cells were counted and the number of background spots was subtracted from all samples. The high number of spots detected after the stimulation with Con A (data not shown) indicate a good condition of the used lymphocytes. For each experimental group of mice the number of spots/1×10$^6$ cells are illustrated in FIG. 6, the standard deviation of ex vivo-stimulated triplicates are given.

Figure 7:
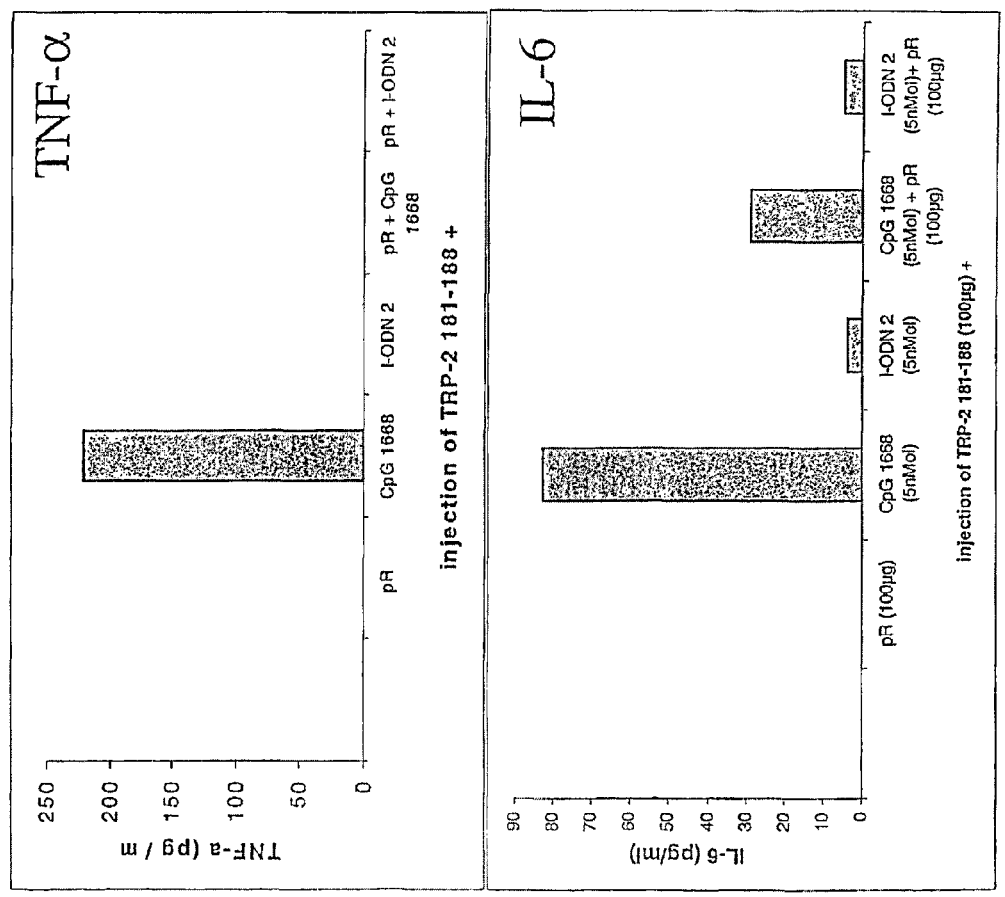
FIG. 7 shows that the combined injection of I-ODN and pR 60 together with a Melanoma-derived peptide reduces the induction of systemic TNF-α and IL-6.

One hour after injection blood was taken from the tail vein and serum was prepared to determine the induction of systemic TNF-α (and IL-6 using specific ELISAs (FIG. 7).

Example 5

The Combined Injection of Random 10-Mer I-ODN and Poly-L-arginine (pR 60) Synergistically Enhances the Immune Response Against a Melanoma-Derived Peptide Experimental Groups (5 Mice Per Group)
1. TRP-2$_{181-188}$
2. TRP-2$_{181-188}$+pR 60
3. TRP-2$_{181-188}$+CpG 1668
4. TRP-2$_{181-188}$+ODN 17
5. TRP-2$_{181-188}$+CpG 1668+pR 60
6. TRP-2$_{181-188}$+ODN 17+pR 60

Figure 8:
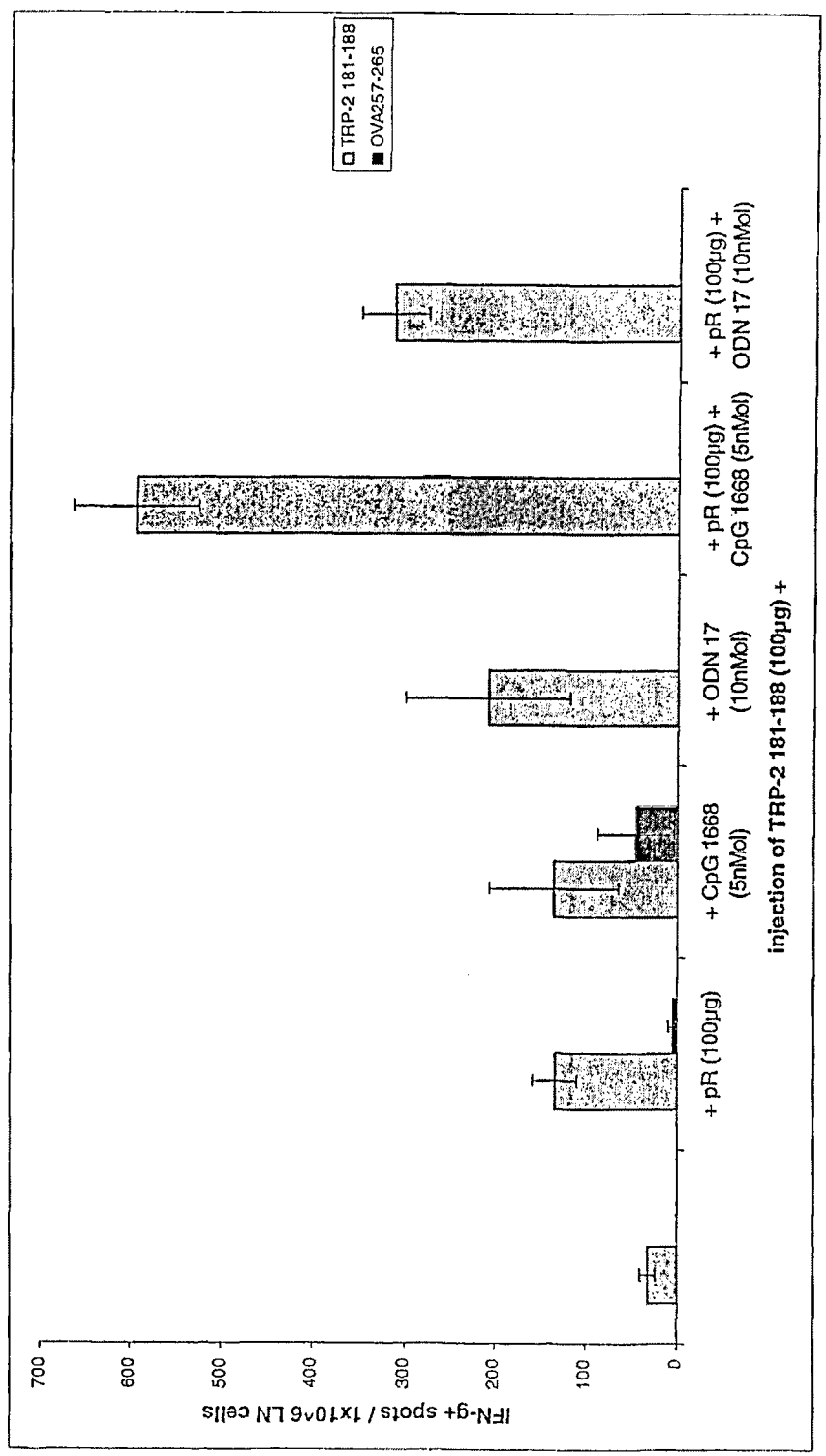
FIG. 8 shows the combined injection of a random 10-mer I-ODN and pR 60 together with a Melanoma-derived peptide.

On day 0 mice were injected into each hind footpad with a total volume of 100 µl (50 µl per footpad) containing the above mentioned compounds. Animals were sacrificed 4 days after injection and popliteal lymph nodes were harvested. Lymph nodes were passed through a 70 µm cell strainer and washed twice with DMEM medium (GIBCO BRL) containing 5% fetal calf serum (FCS, SIGMA chemicals). Cells were adjusted to 3×10$^6$ cells/ml in DMEM/5%/FCS. An IFN-γ ELISPOT assay was carried out in triplicates as described (Miyahira et al., 1995). This method is a widely used procedure allowing the quantification of antigen-specific T cells. Lymphocytes were stimulated ex vivo in triplicates with medium background-control, TRP-2$_{181-188}$-peptide, an irrelevant OVA$_{257-264}$-peptide and Concanavalin A (Con A). Spots representing single IFN-γ producing T cells were counted and the number of background spots was subtracted from all samples. The high number of spots detected after the stimulation with Con A (data not shown) indicate a good condition of the used lymphocytes. For each experimental group of mice the number of spots/1×10$^6$ cells are illustrated in FIG. 8, the standard deviation of ex vivo-stimulated triplicates are given.

| | |
|---|---|
| Mice | C57Bl/6 (Harlan/Olac) |
| Peptide | TRP-2-peptide (VYDFFVWL (SEQ ID NO: 8)), a MHC class I (H-2K$^b$)-restricted epitope of mouse tyrosinase related protein-2 (Bloom et al., 1997) was synthesized by standard solid phase F-moc synthesis, HPLC purified and analyzed by mass spectroscopy for purity. Dose: 100 µg/mouse |
| Poly-L-arginine60 (pR60) | Poly-L-arginine with an average degree of polymerization of 60 arginine residues; SIGMA chemicals Dose: 100 µg/mouse |
| CpG-ODN 1668 | thiophosphate substituted ODNs containing a CpG motif: tcc atg acg ttc ctg atg ct (SEQ ID NO: 7), were synthesized by NAPS GmbH, Göttingen. Dose: 5 nmol/mouse |
| ODN 17 | thiophosphate substituted ODNs containing deoxyinosine: hhh wdi dhh h (SEQ ID NO: 29), were synthesized by NAPS GmbH, Göttingen. (h = CAT, w = AT, d = GAT) Dose: 10 nmol/mouse |
| Mice | C57Bl/6 (Harlan/Olac) |
| Peptide | TRP-2-peptide (VYDFFVWL (SEQ ID NO: 8)), a MHC class I (H-2K$^b$)-restricted epitope of mouse tyrosinase related protein-2 (Bloom et al., 1997) was synthesized by standard solid phase F-moc synthesis, HPLC purified and analyzed by mass spectroscopy for purity. Dose: 100 µg/mouse |
| Poly-L-arginine60 (pR60) | Poly-L-arginine with an average degree of polymerization of 60 arginine residues; SIGMA chemicals Dose: 100 µg/mouse |
| CpG-ODN 1668 | thiophosphate substituted ODNs containing a CpG motif: tcc atg acg ttc ctg atg ct (SEQ ID NO: 7), were synthesized by NAPS GmbH, Göttingen. Dose: 5 nmol/mouse |
| I-ODN 2 | thiophosphate substituted ODNs containing deoxyinosine: tcc atg aci ttc ctg atg ct (SEQ ID NO: |

-continued

| | |
|---|---|
| | 15), were synthesized by NAPS GmbH, Göttingen. Dose: 5 nmol/mouse |

Example 6

The Combined Application of Oligo-deoxyIC$_{26\text{-}mer}$ And Poly-L-arginine (pR) Enhances the Ovalbumin (OVA)-Specific Humoral Response

| | |
|---|---|
| Mice | C57Bl/6 (Harlan/Olac) |
| Ovalbumin (OVA) | Ovalbumin from chicken egg, grade V, SIGMA Chemicals, A-5503, Lot 54H7070 Dose: 50 µg/mouse |
| Poly-L-arginine (pR) | Poly-L-arginine with an average degree of polymerization of 60 arginine residues; SIGMA Chemicals, P-4663, Lot 68H5903 Dose: 100 µg/mouse |
| Oligo-deoxy IC, 26-mer (oligo-dIC$_{26\text{-}mer}$) | oligo-dIC$_{26\text{-}mer}$ (SEQ ID NO: 30) was synthesized by standard phosphoamidide chemistry on a 4 µmol scale and purified by HPLC (NAPS Göttingen, Germany) Dose: 5 nmol/mouse |

Experimental Groups (4 Mice Per Group)
1. OVA+oligo-dIC$_{26\text{-}mer}$+pR
2. OVA+oligo-dIC$_{26\text{-}mer}$
3. OVA+pR
4. OVA On day 0, mice were injected into each hind footpad with a total volume of 100 µl (50 µl per footpad) containing the above listed compounds. On day 24 after injection, serum was collected and screened by ELISA for the presence of OVA-specific antibodies. These results show that the injection of OVA in combination with oligo-dIC and pR enhanced the production of OVA-specific IgG antibodies when compared with injection of OVA with each of the substances alone (FIGS. 9A, 9B). Interestingly, titers of both IgG2a and IgG1 were increased upon one single injection of OVA with oligo-dIC/pR, implying that both Th1 and Th2 cells were involved. However, after 115 days only the increased IgG2a levels were still detectable in sera of mice injected with OVA and oligo-dIC/pR.

These data demonstrate that the combined injection of OVA with oligo-dIC and pR enhances the OVA-specific humoral response. This response is characterized by the production of both Th1- and Th2-induced antibody isotypes in the early phase, but later, mainly by Th1-induced antibodies.

REFERENCES

Andreu, D., and Rivas, L. (1998). Animal antimicrobial peptides: an overview. Biopolymers 47, 415-433.
Ballas, Z. K., Rasmussen, W. L., and Krieg, A. M. (1996). Induction of NK activity in murine and human cells by CpG motif in oligodeoxynucleotides and bacterial DNA. J Immunol 157, 1840-1845.
Bloom, B. R., and Widdus, R. (1998). Vaccine visions and their global impact. Nat Med 4, 480-484.
Bloom, M. B., Perry-Lalley, D., Robbins, P. F., Li, Y., el-Gamil, M., Rosenberg, S. A., and Yang, J. C. (1997). Identification of tyrosinase-related protein 2 as a tumor rejection antigen for the B 16 melanoma. J Exp Med 185, 453-459.
Buschle, M., Schmidt, W., Berger, M., Schaffner, G., Kurzbauer, R., Killisch, 1., Tiedemarm, J. K., Trska, B., Kirlappos, H., Mechtler, K., Schilcher, F., Gabler, C., and Birntsiel, M. L. (1998). Chemically defined, cell-free cancer vaccines: use of tumor antigen-derived peptides or polyepitope proteins for vaccination. Gene Ther. Mol. Biol. 1, 309-321
Buschle, M., Schmidt, W., Zauner, W., Mechtler, K., Trska, B., Kirlappos, H., and Birnstiel, M. L. (1997). Transloading of tumor antigen-derived peptides into antigen-presenting cells. Proc. Natl. Acad. Sci. USA 94, 3256-3261
Cavanaugh, P. F., Jr., Ho, Y-K, and Bardos, T. J. (1996). The activation of murine macrophages and natural killer cells by the Partially thiolated double stranded RNA poly (1). mercapto poly(C). Res. Comm. Mol. Pathol. Pharmacol. 91, 131-147
Chace, J. H., Hooker, N. A., Mildenstein, K. L., Krieg, A. M., and Cowdery, J. S. (1997). Bacterial DNA-induced NK cell IFN-gamma production is dependent on macrophage secretion of IL-12. Clin Immunol Immunopathol 84, 185-193.
Davis, H. L., Weeranta, R., Waldschmidt, T. J., Tygrett, L., Schorr, J., and Krieg, A. M. (1998). CpG DNA is a potent enhancer of specific immunity in mice immunized with recombinant hepatitis B surface antigen. J Immunol 160, 870-876.
Deng, G. M., Nilsson, l. M., Verdrengh, M., Collins, L. V., and Tarkowski, A. (1999). Intra-articularly localized bacterial DNA containing CpG motifs induces arthritis. Nat Med 5, 702-705.
Ganz, T. (1999). Defensins and host defense [comment]. Science 286, 420-421.
Ganz, T., and Lehrer, R. 1. (1999). Antibiotic peptides from higher eukaryotes: biology and applications. Mol Med Today 5, 292-297.
Hancock, R. E. (1999). Host defense (cationic) peptides: what is their future clinical potential? Drugs 57, 469-473.
Harlow, E., and Lane, D. (1988). Antibodies: a laboratory manual (Cold Spring Harbor: Cold Spring Harbor Laboratory).
Hartmann, G., Weiner, G. J., and Krieg, A. M. (1999). CpG DNA: A potent signal for growth, activation, and maturation of human dendritic cells. Proc Natl Acad Sci USA 96, 9305-9310.
Hoffmann, J. A., Kafatos, F. C., Janeway, C. A., and Ezekowitz, R. A. (1999). Phylogenetic perspectives in innate immunity. Science 284, 1313-1318.
Klinman, D. M., Yi, A. K., Beaucage, S. L., Conover, J., and Krieg, A. M. (1996). CpG motifs present in bacteria DNA rapidly induce lymphocytes to secrete interleukin 6, interleukin 12, and interferon gamma. Proc Natl Acad Sci USA 93, 2879-2883.
Krieg, A. M. (1999). CpG DNA: a novel immunomodulator [letter]. Trends Microbiol 7, 64-5.
Krieg, A. M. (1996). An innate immune defense mechanism based on the recognition of CpG motifs in microbial DNA. J Lab Clin Med 128, 128-133.
Krieg, A. M., Yi, A. K., Matson, S., Waldschmidt, T. J., Bishop, G. A., Teasdale, R., Koretzky, G. A., and Klinman, D. M. (1995). CpG motifs in bacterial DNA trigger direct B-cell activation. Nature 374, 546-549.
Krieg, A. M., Yi, A. K., Schorr, J., and Davis, H. L. (1998). The role of CpG dinucleotides in DNA vaccines. Trends Microbiol 6, 23-27.

Lethe, B., van den Eynde, B., van Pel, A., Corradin, G., and Boon, T. (1992). Mouse tumor rejection antigens P815A and P815B: two epitopes carried by a single peptide. Eur J Immunol 22, 2283-2288.

Liljeqvist, S., and Stahl, S. (1999). Production of recombinant subunit vaccines: protein immunogens, live delivery systems and nucleic acid vaccines. J Biotechnol 73, 1-33.

Lipford, G. B., Heeg, K., and Wagner, H. (1998). Bacterial DNA as immune cell activator. Trends Microbiol 6, 496-500.

Manetti, R., Annunziato, F., Tomasevic, L., Gianno, V., Parronchi, P., Romagnani, S, and Maggi, E. (1995). Polyinosinic acid:polycytidylic acid promotes T helper type 1-specific immune responses by stimulating macrophage production of interferon-a and interleukin-12. Eur. J. Immunol. 25, 2656-2660

Mosmann, T. R., Cherwinski, H., Bond, M. W., Giedlin, M. A., and Coffman, R. L. (1986). Two types of murine helper T cell clone. 1. Definition according to profiles of lymphokine activities and secreted proteins. J Immunol 136, 2348-2357.

Nossal, G. (1998). Living up to the legacy. Nat Med 4, 475-476

Oxenius, A., Martinic, M M., Hengartner, H., and Klenerman, P. (1999). CpG-containing oligonucleotides are efficient adjuvants for induction of protective antiviral immune responses with T-cell peptide vaccines. J Virol 73, 4120-4126.

Paillard, F. (1999). CpG: the double-edged sword [comment]. Hum Gene Ther 10, 2089-2090.

Pamer, E. G., Harty, J. T., and Bevan, M. J. (1991). Precise prediction of a dominant class I MHC-restricted epitope of *Listeria monocytogenes*. Nature 353, 852-855.

Parronchi, P., Brugnolo, F., Annunziato, F., Manuelli, C., Sampognaro, S., Mavilia, C., Romagnani, S., and Maggi, E. (1999). Phosphorothioate oligodeoxynucleotides promote the in vitro development of human allergen-specific CD4+ T cells into Thl effectors. J Immunol 163. 5946-5953.

Pisetsky, D. S. (1997). Immunostimulatory DNA: a clear and present danger? Nat Med 3, 829-831.

Pisetsky, D. S. (1999). The influence of base sequence on the immunostimulatory properties of DNA. Immunol Res 19, 35-46.

Rammensee, H. G., Friede, T., Stevanoviic S. (1995), MHC ligands and peptide motifs: first listing. Immunogenetics 41, 178-228

Rodrigues, M., Nussenzweig, R. S., Romero, P., and Zavala, F. (1992). The in vivo cytotoxic activity of CD8+ T cell clones correlates with their levels of expression of adhesion molecules. J Exp Med 175, 895-905.

Roitt, I., Brostoff, J., and Male, D. (1998). Immunology (London: Mosby International Ltd).

Rotzschke, O., Falk, K., Stevanovic, S., Jung, G., Walden, P., and Rammensee, H. G. (1991). Exact prediction of a natural T cell epitope. Eur J Immunol 21, 2891-2894.

Schmidt, W., Buschle, M., Zauner, W., Kirlappos, H., Mechtler, K., Trska, B., and Bimstiel, M. L. (1997). Cell-free tumor antigen peptide-based cancer vaccines. Proc. Natl. Acad. Sci. USA 94, 3262-3267

Schwartz, D. A., Quinn, T. J., Thorne, P. S., Sayeed, S., Yi, A. K., and Krieg, A. M. (1997). CpG motifs in bacterial DNA cause inflammation in the lower respiratory tract, J Clin Invest 100, 68-73.

Shimonkevitz, R., Colon, S., Kappler, J. W., Marrack, P., and Grey, H. M. (1984). Antigen recognition by H2-resctricted T cells 11. A tryptic ovalbumin peptide that substitutes for processed antigen. J Immunol 133, 2067-2074.

Simmaco, M., Mignogna, G., and Barra, D. (1998). Antimicrobial peptides from amphibian skin: what do they tell us? Biopolymers 47, 435-450.

Sparbier, K., and Walden, P. (1999). T cell receptor specificity and mimotopes. Curr Opin Immunol 11, 214-218.

Sparwasser, T., Koch, E. S., Vabulas, R. M., Heeg, K., Lipford, G. B., Ellwart, J. W., and Wagner, H. (1998). Bacterial DNA and immunostimulatory CpG oligonucleotides trigger maturation and activation of murine dendritic cells. Eur J Immunol 28, 2045-2054.

Sparwasser, T., Miethke, T., Lipford, G., Borschert, K., Hacker, H., Heeg, K., and Wagner, H. (1997). Bacterial DNA causes septic shock [letter]. Nature 386, 336-337.

Sparwasser, T., Miethke, T., Lipford, G., Erdmann, A., Hacker, H., Heeg, K., and Wagner, H. (1997). Macrophages sense pathogens via DNA mot)&: induction of tumor necrosis factor-alpha-mediated shock. Eur J Immunol 27, 1671-1679.

Weiner, G. J., Liu, H. M., Wooldridge, J. E., Dahle, C. E., and Krieg, A. M. (1997). Immunostimulatory oligodeoxynucleotides containing the CpG motif are effective as immune adjuvants in tumor antigen immunization. Proc Natl Acad Sci USA 94, 10833-10837.

Yew, N. S., Wang, K. X., Przybylska, M., Bagley, R. G., Stedman, M., Marshall, J., Scheule, R. K., and Cheng, S. H. (1999). Contribution of plasmid DNA to inflammation in the lung after administration of cationic lipid:pDNA complexes. Hum Gene Ther 10, 223-234.

The invention claimed is:

1. A pharmaceutical composition comprising an immunostimulatory oligodeoxynucleotide molecule (ODN) consisting of the sequence oligo-dIC$_{26\text{-}mer}$ (SEQ ID NO:30).

2. The pharmaceutical composition of claim 1, further comprising at least one polycationic peptide.

3. The pharmaceutical composition of claim 2, wherein the polycationic peptide contains at least 2 KLK-motifs separated by a linker of 3 to 7 hydrophobic amino acids.

4. The pharmaceutical composition of claim 1 further comprising at least one antigen, wherein the antigen is derived from a viral or bacterial pathogen, from a fungus or parasite, and/or wherein the antigen is a tumor antigen or an antigen with a putative role in autoimmune disease.

5. The pharmaceutical composition of claim 4, further comprising one or more additional antigens.

6. The pharmaceutical composition of claim 4 wherein the antigen comprises a peptide or protein, a carbohydrate, a lipid, a glycolipid or a pathogen itself.

7. The pharmaceutical composition of claim 6 wherein the peptide or protein is glycosylated, lipidated, glycolipidated or hydroxylated.

8. The pharmaceutical composition of claim 4 wherein the pathogen or fungus is selected from the group comprising human immunodeficiency virus (HIV), hepatitis A and B viruses, hepatitis C virus (HCV), Rous sarcoma virus (RSV), Epstein Barr virus (EBV), Influenza virus, Rotavirus, *Staphylococcus aureus, Chlamydia pneumoniae, Chlamydia trachomatis, Mycobacterium tuberculosis, Streptococcus pneumoniae, Bacillus anthracis, Vibrio cholerae, Plasmodium* sp., *Aspergillus* sp. or *Candida albicans*.

9. The pharmaceutical composition of claim 5 wherein the one or more additional antigens comprise peptides or proteins, carbohydrates, lipids, glycolipids or mixtures thereof, or pathogens themselves.

10. The pharmaceutical composition of claim 9 wherein the peptide or protein is glycosylated, lipidated, glycolipidated or hydroxylated.

11. The pharmaceutical composition of claim 5 wherein the one or more additional antigens are derived from viral or bacterial pathogens, from fungi or parasites, and/or wherein the antigens are tumor antigens or antigens with a putative role in autoimmune disease.

12. The pharmaceutical composition of claim 11 wherein the pathogens or fungi are selected from the group comprising human immunodeficiency virus (HIV), hepatitis A and B viruses, hepatitis C virus (HCV), Rous sarcoma virus (RSV), Epstein Barr virus (EBV), Influenza virus, Rotavirus, *Staphylococcus aureus, Chlamydia pneumoniae, Chlamydia trachomatis, Mycobacterium tuberculosis, Streptococcus pneumoniae, Bacillus anthracis, Vibrio cholerae, Plasmodium* sp., *Aspergillus* sp. or *Candida albicans*.

13. A method of production of the pharmaceutical composition of claim 1, comprising combining the ODN with a pharmaceutically-acceptable carrier.

14. A method of stimulating an immune response comprising administering to a subject in need thereof the pharmaceutical composition of claim 1.

* * * * *